US009382518B2

(12) United States Patent

Dubovi et al.

(10) Patent No.: US 9,382,518 B2

(45) Date of Patent: *Jul. 5, 2016

(54) PNEUMOVIRUS COMPOSITIONS AND METHODS FOR USING THE SAME

(71) Applicant: Cornell University, Ithaca, NY (US)

(72) Inventors: Edward Dubovi, Ithaca, NY (US); Randall W. Renshaw, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,498

(22) Filed: Apr. 24, 2015

(65) Prior Publication Data

US 2015/0299669 A1 Oct. 22, 2015

Related U.S. Application Data

(63) Continuation of application No. 13/518,009, filed as application No. PCT/US2010/061510 on Dec. 21, 2010, now Pat. No. 9,028,834.

(60) Provisional application No. 61/288,401, filed on Dec. 21, 2009.

(51) Int. Cl.

*C12N 7/00* (2006.01)
*A61K 39/155* (2006.01)
*A61K 39/12* (2006.01)
*C07K 14/005* (2006.01)
*A61K 39/00* (2006.01)

(52) U.S. Cl.

CPC . *C12N 7/00* (2013.01); *A61K 39/12* (2013.01); *A61K 39/155* (2013.01); *C07K 14/005* (2013.01); *A61K 39/00* (2013.01); *C12N 2760/18521* (2013.01)

(58) Field of Classification Search

None

See application file for complete search history.

(56) References Cited

U.S. PATENT DOCUMENTS 5,238,834 A * 8/1993 Pruitt ................ C12N 15/1096 435/252.3
6,677,127 B1 1/2004 Li et al.
6,730,305 B1 5/2004 Wertz et al.
9,028,834 B2 * 5/2015 Dubovi ................ A61K 39/12 424/184.1
2004/0175395 A1 9/2004 Corvaia et al.
2005/0089525 A1 4/2005 Cates et al.
2005/0101530 A1 5/2005 Renzi et al.

OTHER PUBLICATIONS

Collin and Graham. Viral and Host Factors in Human Respiratory Syncytial Virus Pathogenesis. J Virol. Mar. 2008; 82(5): 2040-2055.*

NCBI GenBank Assession No. AY743909, Jan. 11, 2005.

Renshaw, R.W., et al., Pneumovirus in Dogs with Acute Respiratory Disease, Emerging Infectious Diseases, Jun. 1, 2010, vol. 16, No. 6, pp. 993-995.

Hsu, K., et al., Immunogenicity of Recombinant Adenovirus-Respiratory Syncytial Virus Vaccines with Adenovirus Types 4, 5, and 7 Vectors in Dogs and a Chimpanzee, The Journal of Infectious Diseases, Oct. 1992, vol. 166, No. 4, pp. 769-775.

Mackay, I.M., et al., Real-time PCR in virology, Nucleic Acids Research, 2002, vol. 30, No. 6, pp. 1292-1305.

Buonavaglia, C., et al., Canine respiratory viruses, Vet. Res. 38, 2007, pp. 355-373.

Thorpe, L.C., et al., Genome sequence of the non-pathogenic strain 15 of pneumonia virus of mice and comparison with the genome of the pathogenic strain J3666, Journal of General Virology, 2005, vol. 86, No. 1, pp. 159-169.

Domachowske, J.B., et al., Differential Expression of Proinflammatory Cytokine Genes In Vivo in Response to Pathogenic and Nonpathogenic Pneumovirus Infections, The Journal of Infectious Diseases, Jul. 1, 2002, vol. 186, pp. 8-14.

* cited by examiner

*Primary Examiner* — Michelle S Horning

(74) *Attorney, Agent, or Firm* — Hodgson Russ LLP

(57) ABSTRACT

Provided are newly identified pneumoviruses that can infect mammals, including dogs cats and potentially humans. Isolated polynucleotides and proteins of the viruses, as well as the isolated viruses themselves are provided. The invention includes compositions and methods for detecting the viruses, methods and compositions for prophylaxis and/or therapy of disease signs that are positively correlated with the presence of the viruses, and isolated cells comprising the viruses. Intact virions, viral proteins, and fragments thereof are also provided.

4 Claims, 3 Drawing Sheets

(Green immunofluorescence)

(Red immunofluorescence produced by counter-staining)

SEQUENCE LISTING

```
<160> NUMBER OF SEQ ID NOS: 48

<210> SEQ ID NO 1
<211> LENGTH: 8598
<212> TYPE: RNA
<213> ORGANISM: Canine pneumovirus

<400> SEQUENCE: 1

ggagguggug gcggugaagu cgucuuucaa gaaaggucua ccaaugauac agcugccaag      60

agcauuaguu ucacuaaaag auauaacacc cuuuaaguag cuaucuggua aguacacauu     120

uacuucuugu ucaucaauag gauccauauu gauccuaauu gauuauuuuu auauaacuau     180

ugaauuaaca ugaaguuggu ugacuuggaa ucuacacgau ugacaauuug agguuaauga     240

cugauagcug acagaugaag gaauacaguc cacaucaucu ggccugacua uaaucaaagu     300

cuaugaucac uugauuacuc cagcugaguu cuaugcagca caaggccucu uucacacagg     360

cuaucacauc gacacgguuc cacaccacag acuucccugc aucuauuauu guggaugguc     420

uagacccauc guaagugagg uuucuauuua cuccaauaau auacaucuua ugcaguaugg     480

cuggauagua uuuaggcagc cuuaucauuc uguuuucaua gaagaauuua ucuucuccuc     540

gauggagaug acagauugga ucagacugca uaauacuccu acuggcaguu ucuugagaau     600

gugaauaacu ugucucuucu uguguaucuu gucuauauaa gauaguauag uguugcaacu     660

ucucaaauaa uugacguccu cugcguugcu aucucuugcu uguauuacca gaccaacauc     720

caaguucugu aacacaguaa ucaaacugcc acaagcuauc gacuuaguga uguuguuagu     780
```

```
uuuuuccagg uaacuuuuca gcacaccuau gguucccaaa gcauacucag caguccuuug    840
uggugcauca aauccacuga caucggucau ugcaucugug uugguaucga ggaaccuaua    900
aauccuauug agcauauagu ucugccugag cauaagaguu uucaaaggcc auucccaaua    960
uuuaugacua uacuugcaau uccucccucu ggaacaaaac ccuugaaccu caaauuugca   1020
aggucucaca cucauccuac ccuguccuug agagucgagg gaaguguugg gucuggauug   1080
ucacuuaucc uaaguuuuuu aauuaacuaa cucaauuaug auuugguaca auugucauga   1140
uaaaacugug aggccaggug uacuuuugga uuucaaccug uuguccuga uaauuuucga   1200
uaccuuauac agaaugaacc cuaugacaac cauuauuaua auaagcauua caacgaugag   1260
cagaguuguu aguauauaug acuugguuaa acuuuuauuc acucuguuuu cacuuaaguc   1320
caauaacuga ucagaggccu ucaagaaugu gcgugucuga uugaugcuau gcuccacauc   1380
ucuuauagca acaucaaauu uaucgucagg gaaauucaaa gggucauauu ucaagaccaa   1440
cgguuccccu cugacuacaa uugacuugcc aacuucuuug cuaagauagu agacaguguu   1500
uccuacuuga accuugucca ccccuuuguu ggagauguag ugacaaccau cuggcagagu   1560
ccuuauuaua ccuuugucau uauugaugac ugugcaacug uuauggccau agcaagacac   1620
caagcaaccc auuguaguca guacugcugu acucacauau guuuuacuug uggaaaucuu   1680
acaaucguag uuagugguau acauguuuga guugcauucu cgugauguua cagguacagu   1740
uagacuuuuc agagugucac agaaaacaua cccauugugg aucucacaau cuguugguga   1800
ugggaaguau gauaaugagc cugcauugug acaauaccag ccauuaucag cucuagccaa   1860
acaagcauau uugucugcua uguuaugaca gucuauggaa cuucuuauua cccaacaauc   1920
uguguccaua acaccaaaua acgggaguug uauuauauaa accagugugu cagcauugac   1980
ugaacuuaau auugcuaacc cguuucuucu cauuauagcu cuacuagaua gcauuaucuc   2040
uuuuuggccu gcugaaacag ccaugccgcc uacuauggag gugaguuccc ggucuguuaa   2100
cauaaaagau gaaacagugu guguuaaucc ugcauuagau gaaaauucac gagacacuuc   2160
caaaagucuu uuguugagcu guuggaaucu aaugacggca gugaugucgu gcacaucaca   2220
agagacucgg uuuauuuuug ggaguaauuc uuuagauaug aaguuuuuca aaucaucuac   2280
cacuuuagcu aacacugaca ugccguuggu uaggcuaaca acagccucau uuguauuucu   2340
cacugcuucu cuaaucaaug caaucucacu uucaaguugc acugucuugg cuaaagccac   2400
cccggcagug acugcagccc cgagaccaag aaucaaaccg aggaaccucu ucuuccuuuu   2460
ggacuucaaa gcauuggaug auaacguucu caauucaucc acugcauuac uauagauugc   2520
aagcucauga gccaauaacg aguugcugcu cuugcaugac ucaauauuua uuugagacaa   2580
cuuaauugac auaacuguca ugugccaacc aguucuaagg gcacucuuau aaccugcagu   2640
cucaacacua cauguggacu cauagaauuu uucuguuaau guauuugggu gaauugguuu   2700
gguguugaag aucaacagaa gaacuagaaa gauccugcca ggaaucauau uuguccuauu   2760
auaucauagc uuauuuuuca uuaacuacug auaagguugg uacuuauucu gaaguugauu   2820
cggguauagg ucacucaaga auuagaccuc cuuggaaaua auuggagcau aggacaccaa   2880
uagggcauug uugguuuggg uucucugcuu gagccuacuc cacauaaagc ucuuuucuuc   2940
cgacugagag guuuggaccu ccuaggugcg gggguugggu ucccugucuc cgguguuggu   3000
gccguggugg ugccugugga uuguuugagu gcagcuuugu gggcuugagg acuuaggcug   3060
gguaguccaa cuagaggaag guuucuugaa agcccaucac augugagaua aaauuuguua   3120
ucuaggccag cugagucugc acagguggua cacugagacu gauucuuguu guuaaaacua   3180
```

-continued

```
ggaaacaaaa ucacaguuug gucugucagg uugcaguuug uucugggaac aacacaauua   3240

gaguuacucc aauaguguuu ccaauaggaa ucauaaugca auuccaugau aacuuguuga   3300

ccuccaagcu cuagcacggc ucucuucuga ucagugcuua aaccagaaag gaagaaacag   3360

aagcccugau cacacccauu guggacacac auugcccuuu uguuggagua cguagaaagg   3420

gugauaaccu cuauauaagg ugcagcuucu ucuccaccac cauuguuuaa gcccauguuu   3480

gccuucauug uuacaagauc agggcaaaca cuuccuaagu ugaucucacg uuucucauaa   3540

caguuggugc ugugauguuc aggaccugga ggcuugcaua gaacauccaa uacgagcuug   3600

aaaucuucag guaaaucagg ucggucuaaa uaaccauugc uggagcauug guagggaucc   3660

ucugagggug ucaccauuuu gacaggcucu gugaucucau ggugggugguu gguuuuggug   3720

gggguuugg ugaguuuggg gguggucccu ugcucugugg ugggcaggcc ggcgguuggu   3780

uggggagggg cggaugugcu guuccggauu guggcguucu gcguggaguu ggccuuguga   3840

uuugauguga auacagaaua cauuaugacc cccacacaaa cugccacagc agcacuugug   3900

agcacaccug caauaagcuu acacauuugg uucacuuuua caacaguccu aaauguguca   3960

ggauacugag uucucucaaa guucaaauua guaaugcugc cacccacuuc aaaguuccuu   4020

cccauacuaa gugaagucaa cuuguaguuc ucuuguauga gcugcucuac aguucucauc   4080

agauuccaau aagauaguac uuauccuaau uuuuuguuaa cuagacgaca uacuacaagg   4140

gcugauugaa ucaccuagca gaguggggcu gucuggcucg ggguuuauug aaggaugguu   4200

uuugcuguuu auaacauuau guaguguucc uugaguacag guugcccggc agacuaguua   4260

cauugauucc auaacuuggu ggagggugau ugggaugaac cgugcauugg cugcuagcga   4320

ugccugaugu agcaaugcuc cuacugcugc aggccauuau cagcgcacac acuguguuga   4380

uaacagcgca ugcaaggaga agagcuguca gggcuagugu aauauaugua ccaauacggc   4440

ugcuggucau guugaucuca aaagugaucu gguaugaggu cauguuagga uccauuacuu   4500

auccuguuuu auuuaacuaa gauaugugug uggauauaug uaggugugua uaugugguug   4560

ucauauggau guugguggca auaguuguug ugcuagguga agucgugggg uuguaguuau   4620

ggauugagcu gaucaauggu gacuuucuau uuuuucaucc acuuguugag gaacucuuga   4680

guauguagga agugccugua uguuuccagu ucauaaucac aucauguagg cucaccugag   4740

ucagauaggg acccaguucu gcaagaauuu gacaaccugc cuuuagcagu uugaaugcac   4800

cuuuggugga ugugauguug aucacaagug ugaguccugc auagggagcc acccuagcug   4860

uuguuauagc augguccaca ucggagcuua uagccugcuc cacacuauca agguccugcu   4920

gucugauaga cagugcucug augaagacag guauagugaa ugacuuuaau guaacccugu   4980

uauggaaaga gcagacagcu aucagcucau gaguaggucg auuaguagga guaaugcugg   5040

gcacagugua aagcauguuu uuaggcuuaa gaauugucac acagaagcuc uuuuuaucaa   5100

aagcaacagg uacuucguau uccauguugc cccagucauc caaggcuaug auagcauuua   5160

ucaagaauug ccuuggcaug guggcuaggc cugcauugga agagcucaga ucuaccuuga   5220

ucaugggacc auguacaguu gauauuugug uacagaugac uguaacauca uguagcaggu   5280

ccaugacaga guuccuuggu agagauguuu gaaacauugg uauccacaca guuagugaua   5340

uguuggcuga auguuuuuca accaaguuua gcuguauugc agcuguauau gggacgccau   5400

gguacaucuc uaccaaguag gccuccauua uuuguccugu uauuuuaauu aacuaaaaau   5460

uaaugcccau gaugucauca acauccaagu cuuccuuagc cuccucagca uugcuggaca   5520
```

-continued

```
cuaucuuauc uaguauccuu gcucugucug uuaaaauaaca ggcugaucca ucaucaguuu   5580
cagcucuaga gcauuccuca ucucugagcu ucuccauggc cgccacucug ucauugacag   5640
ucaagauguc agacuugauc aucucaauaa guucuucucu agugccuaua agggcaucuc   5700
uaaucucauc ucuagcagug guugguccag caguugcuac cauaauggug uuuaaaaggc   5760
cuauuaugua ggacaauuuc uccucuauuc uaucuagucu uuguucuaca gaugaagagc   5820
ccggcucuug guuagucucc ucaaaugaua gauugcuuuc uucaucauaa ccaucagcgg   5880
caaaaguuug cauggucucc uuguacaggc uggcucccaa uccgacaaac uucucuucgg   5940
guuccacaaa ggugaccauc ggcuuccuag uuuucuuagu aucgguauca ucugagcagc   6000
auggcuucuu acuguguucc ggauugucag gaaccucaua gacauguaug gucucuaugu   6060
cagcaucaga uucuuugggc ugcucuuccu uguuuugggg aggugugggu gguggagugg   6120
agggggagu ggaggguuua gugaguuuug cggcggcucu ugggggggag aguuugaaug   6180
agcugcgcaa uaugggggc auguuauauu uggugacaug aguggcagug uucgguauac   6240
cagcuagugg uuuuuccgaa gggaaggauc uauguuugag aaacuccucu gccuucuugu   6300
uggcauccuc accgacaaau ucaggggcaa auuucuccau auuuauccua uauuuuccag   6360
uuuuuaauua aauaucauca ucaggagugu caucaacaau gcucagcugu uggcugauca   6420
gcucucuuuc uucuguaguc aaguucaaug cacuguaguu aauuacauug uuguccuuua   6480
aucuuucugc auaaucuuua gcagcaucaa agaguucucu auucuuagga gcacccuuau   6540
aagacccuau gaugccuaaa ccugcagcau ugccaagcac gacacuggug aaauuaggac   6600
aauuggucaa agagaggagu gaagcuuuug gauuauuucu aauaugauag aauccugccu   6660
ccccuccuug cuucuggca uauucguaaa ccucaaccac cuguuccauc ucagcuugaa   6720
cacuagcaug gccuagcaug auauucuuga cagauuuugc caguaaaccc caccucagca   6780
uaacuugucc ugccccguau gcauucauga agagaccaga aaacagcccc ucaaccuugc   6840
ugccacccuu gacacuagac ugggccaggc caaaagugau gaagacauca auguaauaag   6900
gcuuccuuuc aaacagguca uaaaagcuuu cagcuaucug cuugaccucc agguugggau   6960
aucuggcuuu cucggcuuuc agcacauuua aagcccuucu uuccacagca ucaaguccuc   7020
cucugucucc ugcagcuaau uuggaaacaa cuaaugcugc aacacagaga acuauuacac   7080
cacaaucugg ugcaucaugc cuccgauuau cagguaaccc ggcuccuguu uugaguucuu   7140
uugcuaccac uccucuggcu uguaucucca gaucagcuaa auuggccgca ucuauuccca   7200
cuauaucuag gacuuguauu uuauagucuu uuccuuguaa uuugauugua aaguccuuga   7260
gcugugucuc cacacauuuu acauuguagc cggcuucucu caguauuuug augcugucau   7320
cucugccuaa caaggacaug gcauauugga gcccuaucuc ugccacuucu ucgcagcggu   7380
ugaaagcagu aaguaggaac augccaagug uccuugcaag ggccuucugc auagcaugac   7440
cagauacacu gguuacaucg ccuguggauc ugguaacacu guauuugcag uuggacagca   7500
ggcuauccuu guuugagaca ucauugagcu ucaacuuguc uagagacauu uuggcccggc   7560
uuaggaugug uauuuauccu aauauuuuuc uauaacuaau cauagacuaa auacuguauc   7620
acuugcuaua gguggugga uucucugcug guuggagcga ucugaaucag cucagucauc   7680
aucauccuca uuacagauca agucauggcc uggguacaga augcauccug ugcacucaau   7740
ccagucuucu uugugcugua caaagaagaa cuuuggguau uucuccccag uuacuuucuu   7800
cugccuccuu augcacuucc acucaaugcu gucugccuca gaugccauua ccauccaagc   7860
caugucuucc acauauugcu uggccucaau guaccccauu uuuuccuuuu uaagucuauc   7920
```

```
auugcagauc cugaugaagu uccgguugau guaucuagug auguuuugua agcucggcug   7980

gaauuuuuca augagcaagu caagccaccu cucugagcuc ugugugguac gggacaccuu   8040

gcccaucccu gcuucaucac ucgacucuuc acugucugaa auguucaaga uaguagcagg   8100

uuuagaaaug gucugaguga acuuguucau agcuguggac auuaggauuu guccuacccu   8160

uuguuuuaau uaacuacaua augugcuguc auuuuaacca cugaucagcu cugccaauag   8220

cucacaugug gggucaaugg gaggcucuau cucuugcccu guaggacuaa acacgauauc   8280

uuuugugaac caauguguua auguuuggcc ucuucuagua uuauggauga auuuggcagc   8340

uugcacaaau ggucucaaca aguugcaguc ccuucccacg agguacacgg agagucucug   8400

aucuugccau guacugcaca cccuagcacc ucuuaagauc guuuccaaau cugaccuauu   8460

gaaguugguu auguggaaug ccaaccaugc agcucuucca ccauaaccaa gcuccaucau   8520

cacauuacag cccaugauuc uggucuuuaa gacuaguugu cuccacuugu ccuaacuuuu   8580

ucggaguggu ggguuugg                                                 8598
```

```
<210> SEQ ID NO 2
<211> LENGTH: 354
<212> TYPE: RNA
<213> ORGANISM: Feline pneumovirus

<400> SEQUENCE: 2

ccgugguggu gccuguggau uguuugaguu cagcuuugug ggcuugagga cuuaggcugg     60

guaguccaac uagagggagg uuucuugaaa gcccaucaca ugugagguaa aauuuguuau    120

cuaggccagc ugagucugca caggugguac acugagacug auucuuguug uuaaaacuag    180

gaaacaaaau cacaguuugg ucugucaggu ugcaguuugu ucugggaaca acacaauuaa    240

aguugcucca auaguguuuc caauaggaau cauaaaugcaa uuccaugaua gcuuguugac   300

cuccaagcuc uagcacagcu cucuucugau cagugcuuaa accagaaagg aaga          354
```

```
<210> SEQ ID NO 3
<211> LENGTH: 207
<212> TYPE: RNA
<213> ORGANISM: Feline pneumovirus

<400> SEQUENCE: 3

gauugggaug aacugugcau uggcugcuaa cgaugccuga uguagcaaug cuccuacugc     60

ugcaggccau uaucagcgca cacacugugu ugauaacagc gcaugcaagg aggagagcug    120

ucagggcuag uguaauguau gugccaauac ggcugcuggu cauguugauc ucaaaaguga    180

ucugguguga ggucauguua ggaucca                                        207
```

```
<210> SEQ ID NO 4
<211> LENGTH: 8598
<212> TYPE: RNA
<213> ORGANISM: Canine pneumovirus

<400> SEQUENCE: 4

ccaaacccac cacuccgaaa aaguuaggac aaguggagac aacuagucuu aaagaccaga     60

aucaugggcu guaaugugau gauggagcuu gguuauggug gaagagcugc augguuggca    120

uuccacauaa ccaacuucaa uaggucagau uuggaaacga ucuuaagagg ugcuagggug    180

ugcaguacau ggcaagauca gagacucucc guguaccucg ugggaaggga cugcaacuug    240

uugagaccau uugugcaagc ugccaaauuc auccauaaua cuagaagagg ccaaacauua    300
```

-continued

```
acacauuggu ucacaaaaga uaucguguuu aguccuacag ggcaagagau agagccuccc    360
auugacccca caugugagcu auuggcagag cugaucagug guuaaaauga cagcacauua    420
uguaguuaau uaaaacaaag gguaggacaa auccuaaugu ccacagcuau gaacaaguuc    480
acucagacca uuucuaaacc ugcuacuauc uugaacauuu cagacaguga agagucgagu    540
gaugaagcag ggaugggcaa ggugucccgu accacacaga gcucagagag guggcuugac    600
uugcucauug aaaaauucca gccgagcuua caaaacauca cuagauacau caaccggaac    660
uucaucagga ucugcaauga uagacuuaaa aaggaaaaaa uggguacau ugaggccaag    720
caauaugugg aagacauggc uuggauggua auggcaucug aggcagacag cauugagugg    780
aagugcauaa ggaggcagaa gaaaguaacu ggggagaaau acccaaaguu cuucuuugua    840
cagcacaaag aagacuggau ugagugcaca ggaugcauuc uguacccagg ccaugacuug    900
aucuguaaug aggaugauga ugacugagcu gauucagauc gcuccaacca gcagagaauc    960
ccaccaccua uagcaaguga uacaguauuu agucuaugau uaguuauaga aaaauauuag   1020
gauaaauaca cauccuaagc cgggccaaaa ugucucuaga caaguugaag cucaaugaug   1080
ucucaaacaa ggauagccug cuguccaacu gcaaauacag uguuaccaga uccacaggcg   1140
auguaaccag uguaucuggu caugcuaugc agaaggcccu ugcaaggaca cuuggcaugu   1200
uccuacuuac ugcuuucaac cgcugcgaag aaguggcaga gauagggcuc caauaugcca   1260
uguccuuguu aggcagagau gacagcauca aaauacugag agaagccggc uacaauguaa   1320
aaugugugga cacacagcuc aaggacuuua caaucaaauu acaaggaaaa gacuauaaaa   1380
uacaaguccu agauauagug ggaauagaug cggccaauuu agcugaucug gagauacaag   1440
ccagaggagu gguagcaaaa gaacucaaaa caggagccgg guuaccugau aaucggaggc   1500
augaugcacc agauuguggu guaauaguuc ucuguguugc agcauuaguu guuuccaaau   1560
uagcugcagg agacagagga ggacuugaug cuguggaaag aagggcuuua aaugugcuga   1620
aagccgagaa agccagauau cccaaccugg aggucaagca gauagcugaa agcuuuuaug   1680
accuguuuga aaggaagccu uauuacauug augucuucau cacuuuuggc cuggcccagu   1740
cuagugucaa ggguggcagc aagguugagg ggcuguuuuc uggucucuuc augaaugcau   1800
acggggcagg acaaguuaug cugagguggg guuuacuggc aaaaucuguc aagaauauca   1860
ugcuaggcca ugcuaguguu caagcugaga uggaacaggu gguugagguu uacgaauaug   1920
cccagaagca aggaggggag gcaggauucu aucauauuag aaauaaucca aaagcuucac   1980
uccucucuuu gaccaauugu ccuaauuuca ccagugucgu gcuuggcaau gcugcagguu   2040
uaggcaucau agggucuuau aagggugcuc cuaagaauag agaacucuuu gaugcugcua   2100
aagauuaugc agaaagauua aaggacaaca auguaauuaa cuacagugca uugaacuuga   2160
cuacagaaga aagagagcug aucagccaac agcugagcau uguugaugac acuccugaug   2220
augauauuua auuaaaaacu ggaaaauaua ggauaaaauau ggagaaauuu gccccugaau   2280
uugucgguga ggaugccaac aagaaggcag aggaguuucu caaacauaga uccuucccuu   2340
cggaaaaacc acuagcuggu auaccgaaca cugccacuca ugucaccaaa uauaacaugc   2400
cccccauauu gcgcagcuca uucaaacucu ccccccccaag agccgccgca aaacucacua   2460
aacccuccac uccccccucc acuccaccac ccacaccucc ccaaaacaag gaagagcagc   2520
ccaaagaauc ugaugcugac auagagacca uacaugucua ugagguuccu gacaauccgg   2580
aacacaguaa gaagccaugc ugcucagaug auaccgauac uaagaaaacu aggaagccga   2640
uggucaccuu uguggaaccc gaagagaagu uugucggauu gggagccagc cuguacaagg   2700
```

-continued

```
agaccaugca aacuuuugcc gcugaugguu augaugaaga aagcaaucua ucauuugagg   2760

agacuaacca agagccgggc ucuucaucug uagaacaaag acuagauaga auagaggaga   2820

aauuguccua cauaauaggc cuuuuaaaca ccauuauggu agcaacugcu ggaccaacca   2880

cugcuagaga ugagauuaga gaugcccuua uaggcacuag agaagaacuu auugagauga   2940

ucaagucuga caucuugacu gucaaugaca gaguggcggc cauggagaag cucagagaug   3000

aggaaugcuc uagagcugaa acugaugaug gaucagccug uuauuuaaca gacagagcaa   3060

ggauacuaga uaagauagug uccagcaaug cugaggaggc uaaggaagac uuggauguug   3120

augacaucau gggcauuaau uuuuaguuaa uuaaaaauac aggacaaaua auggaggccu   3180

acuugguaga gauguaccau ggcgucccau auacagcugc aauacagcua aacuugguug   3240

aaaaacauuc agccaacaua ucacuaacug uguggauacc aauguuucaa acaucucuac   3300

caaggaacuc ugucauggac cugcuacaug auguuacagu caucuguaca caaauaucaa   3360

cuguacaugg ucccaugauc aagguagauc ugagcucuuc caaugcaggc cuagccacca   3420

ugccaaggca auucuugaua aaugcuauca uagccuugga ugacuggggc aacauggaau   3480

acgaaguacc uguugcuuuu gauaaaaaga gcuucugugu gacaauucuu aagccuaaaa   3540

acaugcuuua cacugugccc agcauuacuc cuacuaaucg accuacucau gagcugauag   3600

cugucugcuc uuuccauaac aggguuacau uaaagucauu cacuauaccu gucuucauca   3660

gagcacuguc uaucagacag caggaccuug auagugugga gcaggcuaua agcuccgaug   3720

uggaccaugc uauaacaaca gcuagggugg cucccuaugc aggacucaca cuugugauca   3780

acaucacauc caccaaaggu gcauucaaac ugcuaaaggc agguugucaa auucuugcag   3840

aacuggguccc cuaucugacu caggugagcc uacaugaugu gauuaugaac uggaaacaua   3900

caggcacuuc cuacauacuc aagaguuccu caacaagugg augaaaaaau agaaagucac   3960

cauugaucag cucaauccau aacuacaacc ccacgacuuc accuagcaca acaacuauug   4020

ccaccaacau ccauaugaca accacauaua cacaccuaca uauauccaca cacauaucuu   4080

aguuaaauaa aacaggauaa guaauggauc cuaacaugac cucauaccag aucacuuuug   4140

agaucaacau gaccagcagc cguauuggua cauauauuac acuagcccug acagcucuuc   4200

uccuugcaug cgcuguuauc aacacagugu gugcgcugau aauggccugc agcaguagga   4260

gcauugcuac aucaggcauc gcuagcagcc aaugcacggu ucaucccaau caccccuccac  4320

caaguuaugg aaucaaugua acuagucugc cgggcaaccu guacucaagg aacacuacau   4380

aauguuauaa acagcaaaaa ccauccuuca auaaaccccg agccagacag ccccacucug   4440

cuaggugauu caaucagccc uuguaguaug ucgucuaguu aacaaaaaau uaggauaagu   4500

acuaucuuau uggaaucuga ugagaacugu agagcagcuc auacaagaga acuacaaguu   4560

gacuucacuu aguaugggaa ggaacuuuga agugggguggc agcauuacua auuugaacuu  4620

ugagagaacu caguauccug acacauuuag gacuguugua aaagugaacc aaauguguaa   4680

gcuuauugca ggugugcuca caagugcugc uguggcaguu ugugugggggg ucauaaugua  4740

uucuguauuc acaucaaauc acaaggccaa cuccacgcag aacgccacaa uccggaacag   4800

cacauccgcc ccuccccaac caaccgccgg ccugcccacc acagagcaag ggaccacccc   4860

caaacucacc aaaccccccca ccaaaaccac cacccaccau gagaucacag agccugucaa  4920

aauggugaca cccucagagg aucccuacca augcuccagc aaugguuauu uagaccgacc   4980

ugauuuaccu gaagauuuca agcucguauu ggauguucua ugcaagccuc cagguccuga   5040
```

-continued

```
acaucacagc accaacuguu augagaaacg ugagaucaac uuaggaagug uuugcccuga   5100
ucuuguaaca augaaggcaa acaugggcuu aaacaauggu gguggagaag aagcugcacc   5160
uuauauagag guuaucaccc uuucuacgua cuccaacaaa agggcaaugu guguccacaa   5220
ugggugugau cagggcuucu guuucuuccu uucugguuua agcacugauc agaagagagc   5280
cgugcuagag cuuggagguc aacaaguuau cauggaauug cauuaugauu ccuauuggaa   5340
acacuauugg aguaacucua auuguguugu ucccagaaca aacugcaacc ugacagacca   5400
aacugugauu uuguuuccua guuuuaacaa caagaaucag ucucagugua ccaccugugc   5460
agacucagcu ggccuagaua acaaauuuua ucucacaugu gaugggcuuu caagaaaccu   5520
uccucuaguu ggacuaccca gccuaagucc ucaagcccac aaagcugcac ucaaacaauc   5580
cacaggcacc accacggcac caacaccgga gacaaggaac ccaacccccg caccuaggag   5640
guccaaaccu cucagucgga agaaaagagc uuuaugugga guaggcucaa gcagagaacc   5700
caaaccaaca augcccuauu ggugucuau gcuccaauua uuuccaagga ggucuaauuc   5760
uugagugacc uauacccgaa ucaacuucag aauaaguacc aaccuuauca guaguuaaug   5820
aaaaauaagc uaugauauaa uaggacaaau augauuccug gcaggaucuu ucuaguucuu   5880
cuguugaucu ucaacaccaa accaauucac ccaaauacau uaacagaaaa auucuaugag   5940
uccacaugua guguugagac ugcagguuau aagagugccc uuagaacugg uuggcacaug   6000
acaguuaugu caauuaaguu gucucaaaua aauauugagu caugcaagag cagcaacucg   6060
uuauuggcuc augagcuugc aaucuauagu aaugcagugg augaauugag aacguuauca   6120
uccaaugcuu ugaaguccaa aaggaagaag agguuccucg guuugauucu uggucucggg   6180
gcugcaguca cugccggggu ggcuuuagcc aagacagugc aacuugaaag ugagauugca   6240
uugauuagag aagcagugag aaauacaaau gaggcuguug uuagccuaac caacggcaug   6300
ucaguguuag cuaaagugu agaugauuug aaaaacuuca uaucuaaaga auuacuccca   6360
aaaauaaacc gagucucuug ugaugugcac gacaucacug ccgucauuag auuccaacag   6420
cucaacaaaa gacuuuugga agugucucgu gaauuuucau cuaaugcagg auuaacacac   6480
acuguuucau cuuuuauguu aacagaccgg gaacucaccu ccauaguagg cggcauggcu   6540
guuucagcag gccaaaaaga gauaaugcua ucuaguagag cuauaaugag aagaaacggg   6600
uuagcaauau uaaguucagu caaugcugac acacugguuu auauaaauaca acucccguua   6660
uuuggguguua uggacacaga uuguugggua auaagaaguu ccauagacug ucauaacaua   6720
gcagacaaau augcuuguuu ggcuagagcu gauaauggcu gguauuguca caaugcaggc   6780
ucauuaucau acuucccauc accaacagau ugugagaucc acaaugggua uguuuucugu   6840
gacacucuga aaagucuaac uguaccugua acaucacgag aaugcaacuc aaacauguau   6900
accacuaacu acgauuguaa gauuuccaca aguaaaacau augugaguac agcaguacug   6960
acuacaaugg guugcuuggu gucuugcuau ggccauaaca guugcacagu caucaauaau   7020
gacaaaggua uaauaaggac ucugccagau gguugucacu acaucuccaa caaaggggug   7080
gacaagguuc aaguaggaaa cacugucuac uaucuuagca aagaaguugg caagucaauu   7140
guagucagag gggaaccguu ggucuugaaa uaugacccuu ugaauuuccc ugacgauaaa   7200
uuugauguug cuauaagaga uguggagcau agcaucaauc agacacgcac auucuugaag   7260
gccucugauc aguuauugga cuuaagugaa aacagaguga auaaaaguuu aaccaaguca   7320
uauauacuaa caacucugcu caucguugua augcuuauua uaauaauggu ugucauaggg   7380
uucauucugu auaagguauc gaaaauuauc agggacaaca gguugaaauc caaaaguaca   7440
```

```
ccuggccuca caguuuuauc augacaauug uaccaaauca uaauugaguu aguuaauuaa   7500

aaaacuuagg auaagugaca auccagaccc aacacuuccc ucgacucuca aggacagggu   7560

aggaugagug ugagaccuug caaauuugag guucaagggu uuuguuccag agggaggaau   7620

ugcaaguaua gucauaaaua uugggaaugg ccuuugaaaa cucuuaugcu caggcagaac   7680

uauaugcuca auaggauuua uagguuccuc gauaccaaca cagaugcaau gaccgauguc   7740

aguggauuug augcaccaca aaggacugcu gaguaugcuu ugggaaccau aggugugcug   7800

aaaaguuacc uggaaaaaac uaacaacauc acuaagucga uagcuugugg caguuugauu   7860

acuguguuac agaacuugga uguuggucug guaauacaag caagagauag caacgcagag   7920

gacgucaauu auuugagaag uugcaacacu auacuaucuu auauagacaa gauacacaag   7980

aagagacaag uuauucacau ucucaagaaa cugccaguag gaguauuaug cagucugauc   8040

caaucuguca ucuccaucga ggagaagaua aauucuucua ugaaaacaga augauaaggc   8100

ugccuaaaua cuauccagcc auacugcaua agauguauau uauuggagua aauagaaacc   8160

ucacuuacga ugggucuaga ccauccacaa uaauagaugc agggaagucu guggugugga   8220

accgugucga ugugauagcc ugugugaaag aggccuugug cugcauagaa cucagcugga   8280

guaaucaagu gaucauagac uuugauuaua gucaggccag augaugugga cuguauuccu   8340

ucaucuguca gcuaucaguc auuaaccuca aauugucaau cguguagauu ccaagucaac   8400

caacuucaug uuaauucaau aguuauauaa aaauaaucaa uuaggaucaa uauggauccu   8460

auugaugaac aagaaguaaa uguguacuua ccagauagcu acuuaaaggg uguuauaucu   8520

uuuagugaaa cuaaugcucu uggcagcugu aucauuggua gaccuuucuu gaaagacgac   8580

uucaccgcca ccaccucc                                                 8598
```

<210> SEQ ID NO 5
<211> LENGTH: 116
<212> TYPE: PRT
<213> ORGANISM: Feline pneumovirus

<400> SEQUENCE: 5

```
Leu Ser Gly Leu Ser Thr Asp Gln Lys Arg Ala Val Leu Glu Leu Gly
1               5                   10                  15

Gly Gln Gln Ala Ile Met Glu Leu His Tyr Asp Ser Tyr Trp Lys His
            20                  25                  30

Tyr Trp Ser Asn Phe Asn Cys Val Val Pro Arg Thr Asn Cys Asn Leu
        35                  40                  45

Thr Asp Gln Thr Val Ile Leu Phe Pro Ser Phe Asn Asn Lys Asn Gln
    50                  55                  60

Ser Gln Cys Thr Thr Cys Ala Asp Ser Ala Gly Leu Asp Asn Lys Phe
65                  70                  75                  80

Tyr Leu Thr Cys Asp Gly Leu Ser Arg Asn Leu Pro Leu Val Gly Leu
                85                  90                  95

Pro Ser Leu Ser Pro Gln Ala His Lys Ala Glu Leu Lys Gln Ser Thr
            100                 105                 110

Gly Thr Thr Thr
        115
```

<210> SEQ ID NO 6
<211> LENGTH: 68
<212> TYPE: PRT
<213> ORGANISM: Feline pnuemovirus

<400> SEQUENCE: 6

```
Asp Pro Asn Met Thr Ser His Gln Ile Thr Phe Glu Ile Asn Met Thr
1               5                   10                  15

Ser Ser Arg Ile Gly Thr Tyr Ile Thr Leu Ala Leu Thr Ala Leu Leu
            20                  25                  30

Leu Ala Cys Ala Val Ile Asn Thr Val Cys Ala Leu Ile Met Ala Cys
        35                  40                  45

Ser Ser Arg Ser Ile Ala Thr Ser Gly Ile Val Ser Ser Gln Cys Thr
    50                  55                  60

Val His Pro Asn
65
```

<210> SEQ ID NO 7
<211> LENGTH: 113
<212> TYPE: PRT
<213> ORGANISM: Canine pneumovirus

<400> SEQUENCE: 7

```
Met Gly Cys Asn Val Met Met Glu Leu Gly Tyr Gly Gly Arg Ala Ala
1               5                   10                  15

Trp Leu Ala Phe His Ile Thr Asn Phe Asn Arg Ser Asp Leu Glu Thr
            20                  25                  30

Ile Leu Arg Gly Ala Arg Val Cys Ser Thr Trp Gln Asp Gln Arg Leu
        35                  40                  45

Ser Val Tyr Leu Val Gly Arg Asp Cys Asn Leu Leu Arg Pro Phe Val
    50                  55                  60

Gln Ala Ala Lys Phe Ile His Asn Thr Arg Arg Gly Gln Thr Leu Thr
65                  70                  75                  80

His Trp Phe Thr Lys Asp Ile Val Phe Ser Pro Thr Gly Gln Glu Ile
                85                  90                  95

Glu Pro Pro Ile Asp Pro Thr Cys Glu Leu Leu Ala Glu Leu Ile Ser
            100                 105                 110

Gly
```

<210> SEQ ID NO 8
<211> LENGTH: 156
<212> TYPE: PRT
<213> ORGANISM: Canine pneumovirus

<400> SEQUENCE: 8

```
Met Ser Thr Ala Met Asn Lys Phe Thr Gln Thr Ile Ser Lys Pro Ala
1               5                   10                  15

Thr Ile Leu Asn Ile Ser Asp Ser Glu Glu Ser Ser Asp Glu Ala Gly
            20                  25                  30

Met Gly Lys Val Ser Arg Thr Thr Gln Ser Ser Glu Arg Trp Leu Asp
        35                  40                  45

Leu Leu Ile Glu Lys Phe Gln Pro Ser Leu Gln Asn Ile Thr Arg Tyr
    50                  55                  60

Ile Asn Arg Asn Phe Ile Arg Ile Cys Asn Asp Arg Leu Lys Lys Glu
65                  70                  75                  80

Lys Met Gly Tyr Ile Glu Ala Lys Gln Tyr Val Glu Asp Met Ala Trp
                85                  90                  95

Met Val Met Ala Ser Glu Ala Asp Ser Ile Glu Trp Lys Cys Ile Arg
            100                 105                 110

Arg Gln Lys Lys Val Thr Gly Glu Lys Tyr Pro Lys Phe Phe Phe Val
        115                 120                 125
```

```
Gln His Lys Glu Asp Trp Ile Glu Cys Thr Gly Cys Ile Leu Tyr Pro
    130                 135                 140

Gly His Asp Leu Ile Cys Asn Glu Asp Asp Asp Asp
145                 150                 155


<210> SEQ ID NO 9
<211> LENGTH: 393
<212> TYPE: PRT
<213> ORGANISM: Canine pneumovirus

<400> SEQUENCE: 9

Met Ser Leu Asp Lys Leu Lys Leu Asn Asp Val Ser Asn Lys Asp Ser
1               5                   10                  15

Leu Leu Ser Asn Cys Lys Tyr Ser Val Thr Arg Ser Thr Gly Asp Val
            20                  25                  30

Thr Ser Val Ser Gly His Ala Met Gln Lys Ala Leu Ala Arg Thr Leu
        35                  40                  45

Gly Met Phe Leu Leu Thr Ala Phe Asn Arg Cys Glu Glu Val Ala Glu
    50                  55                  60

Ile Gly Leu Gln Tyr Ala Met Ser Leu Leu Gly Arg Asp Asp Ser Ile
65                  70                  75                  80

Lys Ile Leu Arg Glu Ala Gly Tyr Asn Val Lys Cys Val Asp Thr Gln
                85                  90                  95

Leu Lys Asp Phe Thr Ile Lys Leu Gln Gly Lys Asp Tyr Lys Ile Gln
            100                 105                 110

Val Leu Asp Ile Val Gly Ile Asp Ala Ala Asn Leu Ala Asp Leu Glu
        115                 120                 125

Ile Gln Ala Arg Gly Val Val Ala Lys Glu Leu Lys Thr Gly Ala Gly
    130                 135                 140

Leu Pro Asp Asn Arg Arg His Asp Ala Pro Asp Cys Gly Val Ile Val
145                 150                 155                 160

Leu Cys Val Ala Ala Leu Val Val Ser Lys Leu Ala Ala Gly Asp Arg
                165                 170                 175

Gly Gly Leu Asp Ala Val Glu Arg Arg Ala Leu Asn Val Leu Lys Ala
            180                 185                 190

Glu Lys Ala Arg Tyr Pro Asn Leu Glu Val Lys Gln Ile Ala Glu Ser
        195                 200                 205

Phe Tyr Asp Leu Phe Glu Arg Lys Pro Tyr Tyr Ile Asp Val Phe Ile
    210                 215                 220

Thr Phe Gly Leu Ala Gln Ser Ser Val Lys Gly Gly Ser Lys Val Glu
225                 230                 235                 240

Gly Leu Phe Ser Gly Leu Phe Met Asn Ala Tyr Gly Ala Gly Gln Val
                245                 250                 255

Met Leu Arg Trp Gly Leu Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Gln Gly Gly Glu Ala Gly Phe Tyr His Ile Arg
    290                 295                 300

Asn Asn Pro Lys Ala Ser Leu Leu Ser Leu Thr Asn Cys Pro Asn Phe
305                 310                 315                 320

Thr Ser Val Val Leu Gly Asn Ala Ala Gly Leu Gly Ile Ile Gly Ser
                325                 330                 335

Tyr Lys Gly Ala Pro Lys Asn Arg Glu Leu Phe Asp Ala Ala Lys Asp
```

```
            340                 345                 350

Tyr Ala Glu Arg Leu Lys Asp Asn Asn Val Ile Asn Tyr Ser Ala Leu
        355                 360                 365

Asn Leu Thr Thr Glu Glu Arg Glu Leu Ile Ser Gln Gln Leu Ser Ile
    370                 375                 380

Val Asp Asp Thr Pro Asp Asp Asp Ile
385                 390


<210> SEQ ID NO 10
<211> LENGTH: 295
<212> TYPE: PRT
<213> ORGANISM: Canine pneumovirus

<400> SEQUENCE: 10

Met Glu Lys Phe Ala Pro Glu Phe Val Gly Glu Asp Ala Asn Lys Lys
1               5                   10                  15

Ala Glu Glu Phe Leu Lys His Arg Ser Phe Pro Ser Glu Lys Pro Leu
            20                  25                  30

Ala Gly Ile Pro Asn Thr Ala Thr His Val Thr Lys Tyr Asn Met Pro
        35                  40                  45

Pro Ile Leu Arg Ser Ser Phe Lys Leu Ser Pro Pro Arg Ala Ala Ala
    50                  55                  60

Lys Leu Thr Lys Pro Ser Thr Pro Pro Ser Thr Pro Pro Pro Thr Pro
65                  70                  75                  80

Pro Gln Asn Lys Glu Glu Gln Pro Lys Glu Ser Asp Ala Asp Ile Glu
                85                  90                  95

Thr Ile His Val Tyr Glu Val Pro Asp Asn Pro Glu His Ser Lys Lys
            100                 105                 110

Pro Cys Cys Ser Asp Asp Thr Asp Thr Lys Lys Thr Arg Lys Pro Met
        115                 120                 125

Val Thr Phe Val Glu Pro Glu Glu Lys Phe Val Gly Leu Gly Ala Ser
    130                 135                 140

Leu Tyr Lys Glu Thr Met Gln Thr Phe Ala Ala Asp Gly Tyr Asp Glu
145                 150                 155                 160

Glu Ser Asn Leu Ser Phe Glu Glu Thr Asn Gln Glu Pro Gly Ser Ser
                165                 170                 175

Ser Val Glu Gln Arg Leu Asp Arg Ile Glu Glu Lys Leu Ser Tyr Ile
            180                 185                 190

Ile Gly Leu Leu Asn Thr Ile Met Val Ala Thr Ala Gly Pro Thr Thr
        195                 200                 205

Ala Arg Asp Glu Ile Arg Asp Ala Leu Ile Gly Thr Arg Glu Glu Leu
    210                 215                 220

Ile Glu Met Ile Lys Ser Asp Ile Leu Thr Val Asn Asp Arg Val Ala
225                 230                 235                 240

Ala Met Glu Lys Leu Arg Asp Glu Glu Cys Ser Arg Ala Glu Thr Asp
                245                 250                 255

Asp Gly Ser Ala Cys Tyr Leu Thr Asp Arg Ala Arg Ile Leu Asp Lys
            260                 265                 270

Ile Val Ser Ser Asn Ala Glu Glu Ala Lys Glu Asp Leu Asp Val Asp
        275                 280                 285

Asp Ile Met Gly Ile Asn Phe
    290                 295


<210> SEQ ID NO 11
<211> LENGTH: 257
```

<212> TYPE: PRT
<213> ORGANISM: Canine pneumovirus

<400> SEQUENCE: 11

```
Met Glu Ala Tyr Leu Val Glu Met Tyr His Gly Val Pro Tyr Thr Ala
1               5                   10                  15

Ala Ile Gln Leu Asn Leu Val Glu Lys His Ser Ala Asn Ile Ser Leu
            20                  25                  30

Thr Val Trp Ile Pro Met Phe Gln Thr Ser Leu Pro Arg Asn Ser Val
        35                  40                  45

Met Asp Leu Leu His Asp Val Thr Val Ile Cys Thr Gln Ile Ser Thr
    50                  55                  60

Val His Gly Pro Met Ile Lys Val Asp Leu Ser Ser Ser Asn Ala Gly
65                  70                  75                  80

Leu Ala Thr Met Pro Arg Gln Phe Leu Ile Asn Ala Ile Ile Ala Leu
                85                  90                  95

Asp Asp Trp Gly Asn Met Glu Tyr Glu Val Pro Val Ala Phe Asp Lys
            100                 105                 110

Lys Ser Phe Cys Val Thr Ile Leu Lys Pro Lys Asn Met Leu Tyr Thr
        115                 120                 125

Val Pro Ser Ile Thr Pro Thr Asn Arg Pro Thr His Glu Leu Ile Ala
    130                 135                 140

Val Cys Ser Phe His Asn Arg Val Thr Leu Lys Ser Phe Thr Ile Pro
145                 150                 155                 160

Val Phe Ile Arg Ala Leu Ser Ile Arg Gln Gln Asp Leu Asp Ser Val
                165                 170                 175

Glu Gln Ala Ile Ser Ser Asp Val Asp His Ala Ile Thr Thr Ala Arg
            180                 185                 190

Val Ala Pro Tyr Ala Gly Leu Thr Leu Val Ile Asn Ile Thr Ser Thr
        195                 200                 205

Lys Gly Ala Phe Lys Leu Leu Lys Ala Gly Cys Gln Ile Leu Ala Glu
    210                 215                 220

Leu Gly Pro Tyr Leu Thr Gln Val Ser Leu His Asp Val Ile Met Asn
225                 230                 235                 240

Trp Lys His Thr Gly Thr Ser Tyr Ile Leu Lys Ser Ser Ser Thr Ser
                245                 250                 255

Gly
```

<210> SEQ ID NO 12
<211> LENGTH: 92
<212> TYPE: PRT
<213> ORGANISM: Canine pneumovirus

<400> SEQUENCE: 12

```
Met Asp Pro Asn Met Thr Ser Tyr Gln Ile Thr Phe Glu Ile Asn Met
1               5                   10                  15

Thr Ser Ser Arg Ile Gly Thr Tyr Ile Thr Leu Ala Leu Thr Ala Leu
            20                  25                  30

Leu Leu Ala Cys Ala Val Ile Asn Thr Val Cys Ala Leu Ile Met Ala
        35                  40                  45

Cys Ser Ser Arg Ser Ile Ala Thr Ser Gly Ile Ala Ser Ser Gln Cys
    50                  55                  60

Thr Val His Pro Asn His Pro Pro Pro Ser Tyr Gly Ile Asn Val Thr
65                  70                  75                  80

Ser Leu Pro Gly Asn Leu Tyr Ser Arg Asn Thr Thr
```

```
                85                  90


<210> SEQ ID NO 13
<211> LENGTH: 414
<212> TYPE: PRT
<213> ORGANISM: Canine pneumovirus

<400> SEQUENCE: 13

Met Arg Thr Val Glu Gln Leu Ile Gln Glu Asn Tyr Lys Leu Thr Ser
1               5                   10                  15

Leu Ser Met Gly Arg Asn Phe Glu Val Gly Gly Ser Ile Thr Asn Leu
            20                  25                  30

Asn Phe Glu Arg Thr Gln Tyr Pro Asp Thr Phe Arg Thr Val Val Lys
        35                  40                  45

Val Asn Gln Met Cys Lys Leu Ile Ala Gly Val Leu Thr Ser Ala Ala
    50                  55                  60

Val Ala Val Cys Val Gly Val Ile Met Tyr Ser Val Phe Thr Ser Asn
65                  70                  75                  80

His Lys Ala Asn Ser Thr Gln Asn Ala Thr Ile Arg Asn Ser Thr Ser
                85                  90                  95

Ala Pro Pro Gln Pro Thr Ala Gly Leu Pro Thr Thr Glu Gln Gly Thr
            100                 105                 110

Thr Pro Lys Leu Thr Lys Pro Pro Thr Lys Thr Thr Thr His His Glu
        115                 120                 125

Ile Thr Glu Pro Val Lys Met Val Thr Pro Ser Glu Asp Pro Tyr Gln
    130                 135                 140

Cys Ser Ser Asn Gly Tyr Leu Asp Arg Pro Asp Leu Pro Glu Asp Phe
145                 150                 155                 160

Lys Leu Val Leu Asp Val Leu Cys Lys Pro Pro Gly Pro Glu His His
                165                 170                 175

Ser Thr Asn Cys Tyr Glu Lys Arg Glu Ile Asn Leu Gly Ser Val Cys
            180                 185                 190

Pro Asp Leu Val Thr Met Lys Ala Asn Met Gly Leu Asn Asn Gly Gly
        195                 200                 205

Gly Glu Glu Ala Ala Pro Tyr Ile Glu Val Ile Thr Leu Ser Thr Tyr
    210                 215                 220

Ser Asn Lys Arg Ala Met Cys Val His Asn Gly Cys Asp Gln Gly Phe
225                 230                 235                 240

Cys Phe Phe Leu Ser Gly Leu Ser Thr Asp Gln Lys Arg Ala Val Leu
                245                 250                 255

Glu Leu Gly Gly Gln Gln Val Ile Met Glu Leu His Tyr Asp Ser Tyr
            260                 265                 270

Trp Lys His Tyr Trp Ser Asn Ser Asn Cys Val Val Pro Arg Thr Asn
        275                 280                 285

Cys Asn Leu Thr Asp Gln Thr Val Ile Leu Phe Pro Ser Phe Asn Asn
    290                 295                 300

Lys Asn Gln Ser Gln Cys Thr Thr Cys Ala Asp Ser Ala Gly Leu Asp
305                 310                 315                 320

Asn Lys Phe Tyr Leu Thr Cys Asp Gly Leu Ser Arg Asn Leu Pro Leu
                325                 330                 335

Val Gly Leu Pro Ser Leu Ser Pro Gln Ala His Lys Ala Ala Leu Lys
            340                 345                 350

Gln Ser Thr Gly Thr Thr Thr Ala Pro Thr Pro Glu Thr Arg Asn Pro
        355                 360                 365
```

```
Thr Pro Ala Pro Arg Arg Ser Lys Pro Leu Ser Arg Lys Lys Arg Ala
    370                 375                 380

Leu Cys Gly Val Gly Ser Ser Arg Glu Pro Lys Pro Thr Met Pro Tyr
385                 390                 395                 400

Trp Cys Pro Met Leu Gln Leu Phe Pro Arg Arg Ser Asn Ser
                405                 410


<210> SEQ ID NO 14
<211> LENGTH: 537
<212> TYPE: PRT
<213> ORGANISM: Canine pneumovirus

<400> SEQUENCE: 14

Met Ile Pro Gly Arg Ile Phe Leu Val Leu Leu Leu Ile Phe Asn Thr
1               5                   10                  15

Lys Pro Ile His Pro Asn Thr Leu Thr Glu Lys Phe Tyr Glu Ser Thr
            20                  25                  30

Cys Ser Val Glu Thr Ala Gly Tyr Lys Ser Ala Leu Arg Thr Gly Trp
        35                  40                  45

His Met Thr Val Met Ser Ile Lys Leu Ser Gln Ile Asn Ile Glu Ser
    50                  55                  60

Cys Lys Ser Ser Asn Ser Leu Leu Ala His Glu Leu Ala Ile Tyr Ser
65                  70                  75                  80

Asn Ala Val Asp Glu Leu Arg Thr Leu Ser Ser Asn Ala Leu Lys Ser
                85                  90                  95

Lys Arg Lys Lys Arg Phe Leu Gly Leu Ile Leu Gly Leu Gly Ala Ala
            100                 105                 110

Val Thr Ala Gly Val Ala Leu Ala Lys Thr Val Gln Leu Glu Ser Glu
        115                 120                 125

Ile Ala Leu Ile Arg Glu Ala Val Arg Asn Thr Asn Glu Ala Val Val
    130                 135                 140

Ser Leu Thr Asn Gly Met Ser Val Leu Ala Lys Val Val Asp Asp Leu
145                 150                 155                 160

Lys Asn Phe Ile Ser Lys Glu Leu Leu Pro Lys Ile Asn Arg Val Ser
                165                 170                 175

Cys Asp Val His Asp Ile Thr Ala Val Ile Arg Phe Gln Gln Leu Asn
            180                 185                 190

Lys Arg Leu Leu Glu Val Ser Arg Glu Phe Ser Ser Asn Ala Gly Leu
        195                 200                 205

Thr His Thr Val Ser Ser Phe Met Leu Thr Asp Arg Glu Leu Thr Ser
    210                 215                 220

Ile Val Gly Gly Met Ala Val Ser Ala Gly Gln Lys Glu Ile Met Leu
225                 230                 235                 240

Ser Ser Arg Ala Ile Met Arg Arg Asn Gly Leu Ala Ile Leu Ser Ser
                245                 250                 255

Val Asn Ala Asp Thr Leu Val Tyr Ile Ile Gln Leu Pro Leu Phe Gly
            260                 265                 270

Val Met Asp Thr Asp Cys Trp Val Ile Arg Ser Ser Ile Asp Cys His
        275                 280                 285

Asn Ile Ala Asp Lys Tyr Ala Cys Leu Ala Arg Ala Asp Asn Gly Trp
    290                 295                 300

Tyr Cys His Asn Ala Gly Ser Leu Ser Tyr Phe Pro Ser Pro Thr Asp
305                 310                 315                 320

Cys Glu Ile His Asn Gly Tyr Val Phe Cys Asp Thr Leu Lys Ser Leu
                325                 330                 335
```

```
Thr Val Pro Val Thr Ser Arg Glu Cys Asn Ser Asn Met Tyr Thr Thr
            340                 345                 350

Asn Tyr Asp Cys Lys Ile Ser Thr Ser Lys Thr Tyr Val Ser Thr Ala
        355                 360                 365

Val Leu Thr Thr Met Gly Cys Leu Val Ser Cys Tyr Gly His Asn Ser
    370                 375                 380

Cys Thr Val Ile Asn Asn Asp Lys Gly Ile Ile Arg Thr Leu Pro Asp
385                 390                 395                 400

Gly Cys His Tyr Ile Ser Asn Lys Gly Val Asp Lys Val Gln Val Gly
                405                 410                 415

Asn Thr Val Tyr Tyr Leu Ser Lys Glu Val Gly Lys Ser Ile Val Val
            420                 425                 430

Arg Gly Glu Pro Leu Val Leu Lys Tyr Asp Pro Leu Asn Phe Pro Asp
        435                 440                 445

Asp Lys Phe Asp Val Ala Ile Arg Asp Val Glu His Ser Ile Asn Gln
    450                 455                 460

Thr Arg Thr Phe Leu Lys Ala Ser Asp Gln Leu Leu Asp Leu Ser Glu
465                 470                 475                 480

Asn Arg Val Asn Lys Ser Leu Thr Lys Ser Tyr Ile Leu Thr Thr Leu
                485                 490                 495

Leu Ile Val Val Met Leu Ile Ile Ile Met Val Val Ile Gly Phe Ile
            500                 505                 510

Leu Tyr Lys Val Ser Lys Ile Ile Arg Asp Asn Arg Leu Lys Ser Lys
        515                 520                 525

Ser Thr Pro Gly Leu Thr Val Leu Ser
    530                 535
```

```
<210> SEQ ID NO 15
<211> LENGTH: 176
<212> TYPE: PRT
<213> ORGANISM: Canine pneumovirus

<400> SEQUENCE: 15

Met Ser Val Arg Pro Cys Lys Phe Glu Val Gln Gly Phe Cys Ser Arg
1               5                   10                  15

Gly Arg Asn Cys Lys Tyr Ser His Lys Tyr Trp Glu Trp Pro Leu Lys
            20                  25                  30

Thr Leu Met Leu Arg Gln Asn Tyr Met Leu Asn Arg Ile Tyr Arg Phe
        35                  40                  45

Leu Asp Thr Asn Thr Asp Ala Met Thr Asp Val Ser Gly Phe Asp Ala
    50                  55                  60

Pro Gln Arg Thr Ala Glu Tyr Ala Leu Gly Thr Ile Gly Val Leu Lys
65                  70                  75                  80

Ser Tyr Leu Glu Lys Thr Asn Asn Ile Thr Lys Ser Ile Ala Cys Gly
                85                  90                  95

Ser Leu Ile Thr Val Leu Gln Asn Leu Asp Val Gly Leu Val Ile Gln
            100                 105                 110

Ala Arg Asp Ser Asn Ala Glu Asp Val Asn Tyr Leu Arg Ser Cys Asn
        115                 120                 125

Thr Ile Leu Ser Tyr Ile Asp Lys Ile His Lys Lys Arg Gln Val Ile
    130                 135                 140

His Ile Leu Lys Lys Leu Pro Val Gly Val Leu Cys Ser Leu Ile Gln
145                 150                 155                 160

Ser Val Ile Ser Ile Glu Glu Lys Ile Asn Ser Ser Met Lys Thr Glu
```

```
                165                 170                 175


<210> SEQ ID NO 16
<211> LENGTH: 98
<212> TYPE: PRT
<213> ORGANISM: Canine pneumovirus

<400> SEQUENCE: 16

Met Gln Ser Asp Pro Ile Cys His Leu His Arg Gly Glu Asp Lys Phe
1               5                   10                  15

Phe Tyr Glu Asn Arg Met Ile Arg Leu Pro Lys Tyr Tyr Pro Ala Ile
            20                  25                  30

Leu His Lys Met Tyr Ile Ile Gly Val Asn Arg Asn Leu Thr Tyr Asp
        35                  40                  45

Gly Ser Arg Pro Ser Thr Ile Ile Asp Ala Gly Lys Ser Val Val Trp
    50                  55                  60

Asn Arg Val Asp Val Ile Ala Cys Val Lys Glu Ala Leu Cys Cys Ile
65                  70                  75                  80

Glu Leu Ser Trp Ser Asn Gln Val Ile Ile Asp Phe Asp Tyr Ser Gln
                85                  90                  95

Ala Arg


<210> SEQ ID NO 17
<211> LENGTH: 49
<212> TYPE: PRT
<213> ORGANISM: Canine pneumovirus

<400> SEQUENCE: 17

Met Asp Pro Ile Asp Glu Gln Glu Val Asn Val Tyr Leu Pro Asp Ser
1               5                   10                  15

Tyr Leu Lys Gly Val Ile Ser Phe Ser Glu Thr Asn Ala Leu Gly Ser
            20                  25                  30

Cys Ile Ile Gly Arg Pro Phe Leu Lys Asp Asp Phe Thr Ala Thr Thr
        35                  40                  45

Ser


<210> SEQ ID NO 18
<211> LENGTH: 13
<212> TYPE: RNA
<213> ORGANISM: Canine pneumovirus

<400> SEQUENCE: 18

uaguuaauua aaa                                                        13


<210> SEQ ID NO 19
<211> LENGTH: 14
<212> TYPE: RNA
<213> ORGANISM: canine pneumovirus

<400> SEQUENCE: 19

uaguuauaga aaaa                                                       14


<210> SEQ ID NO 20
<211> LENGTH: 14
<212> TYPE: RNA
<213> ORGANISM: canine pneumovirus

<400> SEQUENCE: 20

uauuuaauua aaaa                                                       14
```

<210> SEQ ID NO 21
<211> LENGTH: 13
<212> TYPE: RNA
<213> ORGANISM: canine pneumovirus

<400> SEQUENCE: 21
uaguuaaaua aaa 13

<210> SEQ ID NO 22
<211> LENGTH: 14
<212> TYPE: RNA
<213> ORGANISM: canine pneumovirus

<400> SEQUENCE: 22
uaguuaacaa aaaa 14

<210> SEQ ID NO 23
<211> LENGTH: 14
<212> TYPE: RNA
<213> ORGANISM: canine pneumovirus

<400> SEQUENCE: 23
uaguuaauga aaaa 14

<210> SEQ ID NO 24
<211> LENGTH: 11
<212> TYPE: RNA
<213> ORGANISM: canine pneumovirus

<400> SEQUENCE: 24
cuggaaaaua u 11

<210> SEQ ID NO 25
<211> LENGTH: 16
<212> TYPE: RNA
<213> ORGANISM: canine pneumovirus

<400> SEQUENCE: 25
uaagcuauga uauaau 16

<210> SEQ ID NO 26
<211> LENGTH: 10
<212> TYPE: RNA
<213> ORGANISM: canine pneumovirus

<400> SEQUENCE: 26
aggacaagug 10

<210> SEQ ID NO 27
<211> LENGTH: 10
<212> TYPE: RNA
<213> ORGANISM: canine pneumovirus

<400> SEQUENCE: 27
aggacaaauc 10

<210> SEQ ID NO 28
<211> LENGTH: 10
<212> TYPE: RNA
<213> ORGANISM: canine pneumovirus

<400> SEQUENCE: 28
aggauaaaua 10

<210> SEQ ID NO 29
<211> LENGTH: 10
<212> TYPE: RNA
<213> ORGANISM: canine pneumovirus

<400> SEQUENCE: 29
aggacaaaua 10

<210> SEQ ID NO 30
<211> LENGTH: 10
<212> TYPE: RNA
<213> ORGANISM: canine pneumovirus

<400> SEQUENCE: 30
aggauaagua 10

<210> SEQ ID NO 31
<211> LENGTH: 10
<212> TYPE: RNA
<213> ORGANISM: canine pneumovirus

<400> SEQUENCE: 31
aggauaagug 10

<210> SEQ ID NO 32
<211> LENGTH: 10
<212> TYPE: RNA
<213> ORGANISM: canine pneumovirus

<400> SEQUENCE: 32
aggaucaaua 10

<210> SEQ ID NO 33
<211> LENGTH: 15
<212> TYPE: RNA
<213> ORGANISM: canine pneumovirus

<400> SEQUENCE: 33
uaguuaauua aaaaa 15

<210> SEQ ID NO 34
<211> LENGTH: 14
<212> TYPE: RNA
<213> ORGANISM: canine pneumovirus

<400> SEQUENCE: 34
uaguuauaua aaaa 14

<210> SEQ ID NO 35
<211> LENGTH: 25
<212> TYPE: DNA
<213> ORGANISM: artificial sequence
<220> FEATURE:
<223> OTHER INFORMATION: degenerate primer sequence

<400> SEQUENCE: 35
tccgtgcagg ccgaratgga rcarg 25

<210> SEQ ID NO 36
<211> LENGTH: 25
<212> TYPE: DNA
<213> ORGANISM: artificial sequence
<220> FEATURE:

<223> OTHER INFORMATION: degenerate primer

<400> SEQUENCE: 36
ggaactcggg ggcgaaytty tccat 25

<210> SEQ ID NO 37
<211> LENGTH: 24
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t

<400> SEQUENCE: 37
ccggatcttc ggccayccna tggt 24

<210> SEQ ID NO 38
<211> LENGTH: 29
<212> TYPE: DNA
<213> ORGANISM: artificial sequence
<220> FEATURE:
<223> OTHER INFORMATION: degenerate primer

<400> SEQUENCE: 38
ttcttaggag gggagatggc yttrtcrtt 29

<210> SEQ ID NO 39
<211> LENGTH: 30
<212> TYPE: DNA
<213> ORGANISM: artificial sequence
<220> FEATURE:
<223> OTHER INFORMATION: degenerate primer

<400> SEQUENCE: 39
catcaccgac ctgtccaagt tyaaycargc 30

<210> SEQ ID NO 40
<211> LENGTH: 29
<212> TYPE: DNA
<213> ORGANISM: artificial sequence
<220> FEATURE:
<223> OTHER INFORMATION: degenerate primer

<400> SEQUENCE: 40
ttgaagtcgt ccaggatggt rttdatcca 29

<210> SEQ ID NO 41
<211> LENGTH: 23
<212> TYPE: DNA
<213> ORGANISM: artificial sequence
<220> FEATURE:
<223> OTHER INFORMATION: primer

<400> SEQUENCE: 41
ggcttctgtt tcttcctttc tgg 23

<210> SEQ ID NO 42
<211> LENGTH: 17
<212> TYPE: DNA
<213> ORGANISM: artificial sequence
<220> FEATURE:
<223> OTHER INFORMATION: primer

<400> SEQUENCE: 42
ccgtggtggt gcctgtg 17

<210> SEQ ID NO 43
<211> LENGTH: 24
<212> TYPE: DNA
<213> ORGANISM: artificial sequence
<220> FEATURE:
<223> OTHER INFORMATION: degenerate primer

<400> SEQUENCE: 43
atggatccta acatgacctc ayac 24

<210> SEQ ID NO 44
<211> LENGTH: 22
<212> TYPE: DNA
<213> ORGANISM: artificial sequence
<220> FEATURE:
<223> OTHER INFORMATION: degenerate primer

<400> SEQUENCE: 44
gattgggatg aacygtgcat tg 22

<210> SEQ ID NO 45
<211> LENGTH: 23
<212> TYPE: DNA
<213> ORGANISM: artificial sequence
<220> FEATURE:
<223> OTHER INFORMATION: primer

<400> SEQUENCE: 45
tgtaaaagtg aaccaaatgt gta 23

<210> SEQ ID NO 46
<211> LENGTH: 22
<212> TYPE: DNA
<213> ORGANISM: artificial sequence
<220> FEATURE:
<223> OTHER INFORMATION: primer

<400> SEQUENCE: 46
aaatcttcag gtaaatcagg tc 22

<210> SEQ ID NO 47
<211> LENGTH: 21
<212> TYPE: DNA
<213> ORGANISM: artificial sequence
<220> FEATURE:
<223> OTHER INFORMATION: primer

<400> SEQUENCE: 47
ttttaacaac aagaatcagt c 21

<210> SEQ ID NO 48
<211> LENGTH: 20
<212> TYPE: DNA
<213> ORGANISM: artificial sequence
<220> FEATURE:
<223> OTHER INFORMATION: primer

<400> SEQUENCE: 48
ctcctaggtg cgggggttgg 20

PNEUMOVIRUS COMPOSITIONS AND METHODS FOR USING THE SAME

CROSS-REFERENCE TO RELATED APPLICATIONS

This application is a continuation of U.S. application Ser. No. 13/518,009, filed Jun. 21, 2012, which is the National Phase of International application no. PCT/US2010/061510, filed Dec. 21, 2010, which claims priority to U.S. application No. 61/288,401, filed Dec. 21, 2009, the disclosures of each of which are incorporated herein by reference.

FIELD OF THE INVENTION

The present invention relates generally to the field of virology and more specifically to newly discovered viruses in the family Paramyxoviridae, subfamily Pneumovirinae found in mammals, including canines and felines.

BACKGROUND OF THE INVENTION

Domestic dogs confined together, as in shelters, boarding kennels, or breeding facilities, are often affected with acute respiratory infections (kennel cough). The disease is transmitted rapidly and is difficult to eliminate as new animals are continually introduced. A spectrum of agents may produce a complex syndrome of multiple and sequentially overlapping infections making diagnosis and treatment difficult. Affected dogs have clinical signs ranging from mild dry cough and nasal discharge to pneumonia and death in severe cases. Cats are also infected with various agents that produce respiratory distress of varying degrees of severity. The same or similar viruses may also infect humans. Thus, there is an ongoing and unmet need to identify the agents that infect a variety of mammals and to develop compositions and methods for use in diagnosis, prophylaxis and/or therapy for such infections. The present invention meets these needs.

SUMMARY OF THE INVENTION

The present invention is based on our discovery of novel pneumoviruses. The viruses can infect different types of mammals, including but not necessarily limited to dogs, cats, and likely humans. The presence of the virus can be positively correlated with acute respiratory disease of canines (ARDC), or with respiratory disease in felines, or with respiratory or other disorders in humans or other mammals.

The invention provides isolated polynucleotides and proteins of the viruses, as well as the isolated viruses themselves. The invention includes compositions and methods for detecting the viruses, and methods and compositions for prophylaxis and/or therapy of disease signs that are positively correlated with the presence of the viruses. Also provided are isolated cells that comprise the virus(es).

The viruses of the invention are negative stranded RNA viruses. The invention includes isolated negative strands, the positive strands which have reverse complementarity to the negative strands, the DNA equivalents of the RNA polynucleotides, proteins that are encoded by the positive strands, and fragments of the polynucleotides and the proteins.

In certain embodiments, the isolated viruses contain a negative strand polynucleotide that comprises the sequence of SEQ ID NO:1 or a sequence that is at least 96% identical to the sequence of SEQ ID NO:1. Also provided are isolated polynucleotides that comprise the sequence of SEQ ID NO:2 or SEQ ID NO:3, or a polynucleotide that has a sequence that is at least 96% identical to the sequence of SEQ ID NO:2 or 3.

The invention provides a method of stimulating an immune response in a mammal. The stimulated immune response can be cell-mediated, humoral, or combinations thereof, and can provide a prophylactic and/or therapeutic benefit to the animal. The method of stimulating an immune response comprises administering to a mammal a composition comprising a polynucleotide and/or virus described herein, a viral protein encoded by the viral polynucleotides disclosed herein, a fragment of such a protein, or combinations thereof. The polynucleotides, viruses and/or the proteins and/or fragments thereof can be isolated from any suitable source, or they can be produced recombinantly using well known techniques.

The invention provides a method for detecting the presence of the virus in a biological sample obtained from a mammal. The method comprises obtaining a biological sample from a mammal and detecting from the biological sample a polynucleotide sequence comprised by the virus, or a viral protein or fragment thereof. The presence of the polynucleotide, protein, protein fragment or combination thereof is indicative that the mammal is infected with the virus.

DESCRIPTION OF THE INVENTION

Figure 1:
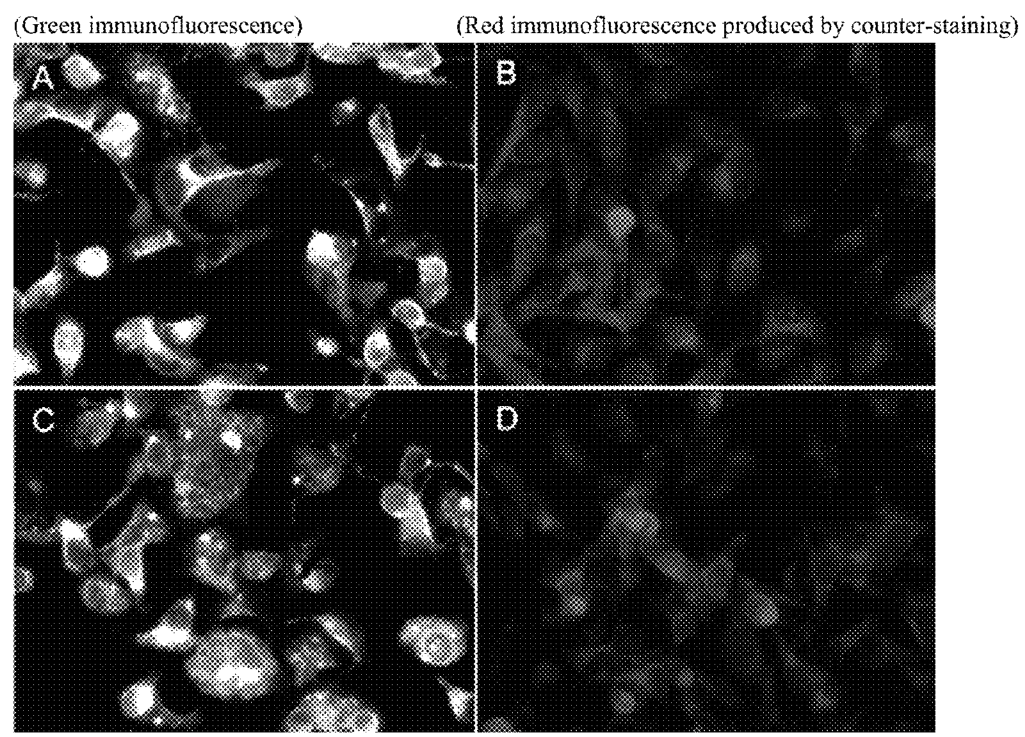
FIG. 1. Immunofluorescence assay of A72 cells using human respiratory syncytial virus-specific monoclonal antibodies (Mab). A) Mab 2G122 on infected cells. B) Mab 2G122 on uninfected cells. C) Mab 5H5N on infected cells. D) Mab 5H5N on uninfected cells. Primary Mab stocks were used as obtained from the manufacturer at a dilution of 1:100. The red background is produced by counter-staining with Evan's Blue.

The present invention provides novel isolated viruses, isolated polynucleotides and proteins of the viruses, compositions and methods for detecting the viruses, and compositions and methods for prophylaxis and/or therapy of disease signs that are positively correlated with the presence of the viruses in a mammal.

The viruses of the invention are negative (minus) stranded RNA viruses. Thus, the genetic material as packaged in the virion is a single strand of RNA that is the reverse complement of a positive strand. The positive strand is transcribed from the negative strand by an RNA-dependent RNA polymerase. The positive strand functions at least in part as an mRNA in that the viral proteins encoded by the positive strand are translated in the cytoplasm of infected cells, and thereafter participate in the assembly of new viral particles and packaging of the minus stranded genomes.

In certain embodiments the invention provides isolated viruses that contain a negative strand polynucleotide that comprises the sequence of SEQ ID NO:1 or a sequence that is at least 96% identical to the sequence of SEQ ID NO:1. The invention also includes polynucleotides which are complementary to the negative strand. In certain embodiments, these polynucleotides comprise the sequence presented in SEQ ID NO:4, or a sequence that is at least 96% identical to SEQ ID NO:4. Also provided are isolated polynucleotides that comprises the sequence of SEQ ID NO:1 or a sequence that is at least 96% identical to the sequence of SEQ ID NO:1, or which comprise the sequence of SEQ ID NO:4, or a sequence that is at least 96% identical to SEQ ID NO:4. Also provided are polynucleotides that comprise the sequence of SEQ ID NO:2 and/or SEQ ID NO:3, or a polynucleotide that has a sequence that is at least 96% identical to the sequence of SEQ ID NO:2 or 3. The reverse complements of these sequences and sequences that have at least 96% identity to the reverse complements are also provided. Combinations of all of the polynucleotides and proteins and fragments thereof disclosed herein are also included in the invention. The viral polynucleotides provided by the invention can be characterized in that they can function to support replication in live viruses (including attenuated viruses).

Also provided are cells that contain the viruses. In various embodiments, the cells that comprise the viruses are isolated cell, or cells that are propagated in vitro for attenuating the viruses, and/or as a source of the viruses for use as vaccines or for other purposes. Thus, isolated cells comprising the viruses, cell cultures and/or cell lines comprising the viruses, viruses and/or viral products present in cell culture medium, and isolated tissues comprising the viruses are all aspects of the invention.

In particular embodiments, the DNA equivalent of each RNA sequence described in the invention is provided. Thus, the invention includes each RNA sequence described herein where each U (uracil) in the RNA is replaced by T (thymine). Each of the viral polynucleotides described in this invention includes polynucleotides that are identical to the sequence presented in the SEQ ID NO designated for each polynucleotide, and further include all polynucleotides that are at least 96% identical to the sequences presented in the viral SEQ ID NOs. In particular embodiments, the polynucleotides that are at least 96% identical to the polynucleotide sequences presented in the sequence listing are at least 96% identical to those sequences across their entire length. Without intending to be bound by any particular theory, it is considered that polynucleotides sequences presented herein and including those having at least 96% identity to the viral polynucleotide sequences set forth in the sequence listing are distinct from the polynucleotides that are comprised by related viruses, such as viruses that are already known to infect murine mammals. It is also considered, again without intending to be bound by any particular theory, that attenuation of the viruses by, for instance, serial passaging, can result in viruses that comprise and/or transcribe polynucleotides that are at least 96% identical to the sequences presented in the sequence listing. The sequences that are not identical to the sequences specifically recited in the sequence listing can be between 96.0% to 99.9% identical to the presented sequences, including all integers to the first decimal point there between. All ranges of sequence identity between 96.0% to 100%, inclusive, are also embodiments of the invention.

Fragments of the polynucleotides are also included in the invention. Thus, in various embodiments, each viral polynucleotide (including the reverse complements and DNA equivalents thereof) includes fragments of the polynucleotides ranging in length from 10 nucleotides to the entire length of the polynucleotide, and including all integers there between. For instance, the invention includes polynucleotides comprising the sequence of SEQ ID NO:1 and including all fragments of that sequence that are between and include 10 nucleotides, up to 8,598 nucleotides in length, and including all integers there between. The polynucleotides provided by the invention, whether or not present in virions, can be longer than those described herein, since the presented sequences may not include the sequence of the entire viral genomes and/or the reverse complements and/or DNA equivalents thereof.

The invention also provides a method of stimulating an immune response in a mammal. The stimulated immune response is an immune response that can provide a prophylactic and/or therapeutic benefit to the animal. The stimulated immune response can be a humoral and/or a cell-mediated immune response. The stimulated immune response can be directed against any antigen and/or immunogen encoded by the virus. Thus, intact viral particles, each viral protein, and fragments of the viral proteins are embodiments of the invention that can be used for stimulating immune responses in mammals. In various embodiments, the animals in which the immune response is stimulated are *Canis familiaris* or *Felis catus*, i.e., domesticated dogs or cats, respectively.

In particular embodiments, the polynucleotide that comprises the sequence of SEQ ID NO:1 or a sequence that is at least 96% identical to the sequence of SEQ ID NO:1, or a protein or protein fragment encoded therein, or a viral particle encoded by the reverse complement of SEQ ID NO:1, is used to stimulate an immune response in a canine. The polynucleotide that comprises the sequence of SEQ ID NO:2 and/or SEQ ID NO:3, or a polynucleotide that has a sequence that is at least 96% identical to the sequence of SEQ ID NO:2 or 3, or a protein or protein fragment or a viral protein encoded by the reverse complement of SEQ ID NO:2 or 3 or a polynucleotide that has a sequence that is at least 96% identical to the reverse complement of SEQ ID NO:2 or 3, are preferably used to stimulate an immune response in felines. The same relationship between these sequences, proteins, protein fragments, and viral particles to the canines and felines applies to the use of these compositions for diagnostic purposes, but this does not in any way diminish the suitability for practicing the invention on other mammals, including humans.

The method of stimulating an immune response comprises administering to the mammal a composition comprising a virus described herein, a viral protein encoded by the viral polynucleotides disclosed herein, a fragment of such a protein, or combinations thereof. The viruses and/or the proteins and/or fragments thereof can be isolated from any suitable source, or they can be produced recombinantly using well known techniques. In various embodiments, the viral proteins provided by the invention for use in vaccines include but are not necessarily limited to the NS-1, NS-2, N, P, M, SH, G, F, M2-1, M2-2, L proteins, and combinations thereof. All nucleotide sequences encoding these proteins are included in the invention and can be determined by those skilled in the art using routine techniques.

The mammal to which a composition of the invention is administered can be any mammal that is at risk for, is suspected of having, or has been diagnosed with a condition that is positively correlated with the presence of one or more pneumonoviruses, including but not necessarily limited to the viruses disclosed herein. In one embodiment, the animal is a dog that is at risk for, is suspected of having or has been diagnosed with ARDC. In another embodiment, the mammal is a human that is at risk for, is suspected of having or is diagnosed with a respiratory disorder or any other disorder that can be positively associated with a virus described herein. In this regard, it is known in the art that viruses related to the newly discovered viruses described herein, such as murine pneumonia virus, can result in widespread infection of humans (See, for example, Pringle C R, Eglin R P. Murine pneumonia virus: seroepidemiological evidence of widespread human infection. J Gen Virol. 1986 June; 67 (Pt 6):975-82). Therefore, it is reasonable to consider the presently provided compositions and methods to have utility for stimulating immune responses in humans and for use in diagnosis of viral infections in humans.

The administration of a composition of the invention, i.e., a vaccine, to an animal can result in a prophylactic effect, meaning that the probability of infection is lower in animals that have received the vaccine relative to animals that have not, or the signs of disease that are positively correlated with the presence of the virus in the animal are less severe relative to an animal that has not received the vaccine. The administration of a vaccine of the invention can also have a therapeutic effect, meaning that the degree of infection (i.e., viral load or titer and/or other markers of degree of infection that are known to those skilled in the art) is lower in an infected animal subsequent to receiving the vaccine relative to an infected animal that does not receive the vaccine Likewise, the signs of disease that are positively correlated with the presence of the virus in the animal can be less severe in an infected animal that has received the vaccine relative to an animal that has not.

The viruses and/or the proteins and the polynucleotides described herein can be isolated, meaning they have been removed from their natural environment by, for example, separating the viruses from an animal and/or a biological sample obtained from the animal. In one embodiment, an isolated cell comprising a virus disclosed herein is considered to encompass an isolated virus. Further, the isolated viruses and/or proteins and/or fragments thereof and/or the isolated and/or recombinant polynucleotides of the invention can be purified to any desired degree of purification. Compositions provided by the invention may comprise, consist or consist essentially of the viruses, viral proteins, fragment(s) thereof, and/or polynucleotides, fragments of the polynucleotides and/or combinations thereof.

In one embodiment, the method comprises administering to a canine a composition that comprises a polynucleotide comprising the sequence of SEQ ID NO:1 or a polynucleotide that has a sequence that is at least 96% identical to the sequence of SEQ ID NO:1, such that an immune response directed against the virus is stimulated in the canine. In one embodiment, the polynucleotide is administered as a DNA vaccine. Methods for making, formulating pharmaceutical compositions comprising, and administering compositions comprising DNA vaccines are known in the art. In one embodiment, the polynucleotide that is administered to the canine is present in a viral particle. The viral particle can be isolated and/or recombinant. In various embodiments, the virus that is administered to the canine contains a protein that comprises an amino acid sequence that is part of a protein comprised by the viral particle. Predicted amino acid sequences of viral proteins comprised by the viral particle as encoded by the viral genome include the canine viral protein NS1, non-structural protein 1 (SEQ ID NO:7), NS2, non-structural protein 2 (SEQ ID NO:8), N, nucleoprotein (SEQ ID NO:9), P, phosphoprotein (SEQ ID NO:10), M, matrix protein (SEQ ID NO:11), SH, small hydrophobic protein (SEQ ID NO:12), G, attachment protein (SEQ ID NO:13), F, fusion protein (SEQ ID NO:14), M2, matrix proteins M2-1 (SEQ ID NO:15) and M2-2 (SEQ ID NO:16), L, RNA-dependent RNA polymerase, for which a partial sequence is provided (SEQ ID NO:17). Feline virus versions of these proteins are also provided by the invention.

In another embodiment, the method comprises administering to a feline a virus with a composition that contains a polynucleotide comprising the sequence of SEQ ID NO:2 and/or SEQ ID NO:3, or a polynucleotide that has a sequence that is at least 96% identical to the sequence of SEQ ID NO:2 or 3, such that an immune response directed against the virus is stimulated in the feline. In one embodiment, the polynucleotide that is administered to the feline is present in a viral particle. The particle can be isolated and/or recombinant.

In various embodiments, the virus that is administered to the feline contains a protein that comprises an amino acid sequence that is selected from SEQ ID NO:5 or SEQ ID NO:6.

In certain embodiments, the present invention comprises a vaccine which can provide a prophylactic and/or therapeutic effect directed against infection by a virus disclosed herein. The vaccine can contain live or killed (inactivated) virus or fragments thereof. Killed viruses are viruses that cannot replicate. Killed viruses can be prepared using any of a variety of techniques that are well known to those skilled in the art, which include but are not limited to heat inactivation and modification of viral proteins and/or nucleic acids, which methods can include but are not necessarily limited to exposure to paraformaldehyde, formalin and ultraviolet light. For example, viral proteins can be covalently modified by, for instance, cross-linking agents which can modify viral proteins so as to prevent one or more steps required for viral cellular entry and/or replication. Live viruses are considered to include attenuated viruses. Attenuated viruses are those that have reduced virulence relative to their unattenuated form. Thus, attenuated viruses can replicate, but only slowly relative to unattenuated viruses of the same type, and thus generally do not cause disease. Those skilled in the art will recognize these and other distinctions between unattenuated, attenuated and killed viruses such that they can be differentiated from one another.

Attenuation of a virus can be obtained using any standard technique. In one embodiment, the virus is attenuated by serial passaging in mammalian cell culture. Serial passaging can result in attenuation through a variety of mechanisms. Any cells that support replication of the virus, including but not limited to human cells, can be used in passaging for the purposes of viral propagation and/or attenuation. In various non-limiting examples, the cell cultures for passaging can be obtained or derived from canines or felines, such as from *Canis familiaris* or *Felis catus*, respectively. In one embodiment, the cells are primary cell cultures. In one embodiment, the cells are comprised by the canine derived A-72 cell line which has American Type Culture Collection (ATCC) catalog number CRL-1542. Any number of passages suitable for viral attenuation can be used. Those skilled in the art will be able to determine passaging parameters for attenuation of the viruses given the benefit of the present disclosure. In general, between 5-150, including all integers there between, and preferably between 20-50 passages may be used.

Compositions containing viruses can be provided as pharmaceutical preparations for use as vaccines. Compositions containing viruses can be prepared as a suspension or in a lyophilized form and can additionally contain pharmaceutically acceptable carriers and/or diluents customarily used for such compositions. Some examples of carriers and diluents suitable for use with the invention can be found in: *Remington: The Science and Practice of Pharmacy* (2005) 21st Edition, Philadelphia, Pa. Lippincott Williams & Wilkins Specific non-limiting examples of carriers include stabilizers, preservatives and buffers. Specific non-limiting examples of stabilizers include carbohydrates (such as sorbitol, mannitol, starch, sucrose, dextran, glutamate or glucose), proteins (such as dried milk serum, albumin or casein) or degradation products thereof. Suitable specific non-limiting examples of buffers include alkali metal phosphates. Suitable specific non-limiting examples of preservatives are thimerosal, merthiolate and gentamicin. Suitable specific non-limiting examples of diluents include water, aqueous buffer (such as buffered saline), alcohols and polyols (such as glycerol).

Those skilled in the art will recognize that the vaccine preparations provided herein can comprise one or more compounds with adjuvant activity. Suitable adjuvants include but are not necessarily limited to Freund's incomplete adjuvant, threonyl muramyl dipeptide, aluminium hydroxide, -phosphate or -oxide, oil-in-water or water-in-oil emulsion based on, for example a mineral oil or a vegetable oil such as vitamin E acetate, and saponins.

The vaccines provided by the invention can be administered via any suitable route. In various embodiments, the vaccines can be administered parenterally, intramuscularly or subcutaneously, intravenously, or orally, including but not necessarily limited to nasally. Those skilled in the art will recognize that effective amounts of the vaccines can be determined using ordinary considerations, such as the type, size, age, environment, risk for or stage of infection, of the animal in which the stimulated immune response is desired. In general, live vaccines according to the invention can be administered in a dose of $10^1$-$10^6$ plaque forming units (pfu) per animal, at for example a 1 ml dose. Inactivated vaccines may contain the antigenic equivalent of $10^6$-$10^{10}$ pfu per animal.

The polynucleotides of the invention may be modified to carry a heterologous gene/genes, which can, for example, provide for immunization against not only the viruses disclosed herein, but also against other related or non-related viruses and/or other infectious agents. Likewise, the vaccine formulations provided herein can also comprise immunogenic agents that are intended to stimulate immune response against infectious agents that are distinct from the viruses disclosed herein. Thus, the invention contemplates combination vaccines for use in diverse mammals and against diverse infectious agents. The combination vaccines can include fusion proteins which comprise all or a portion of the viral proteins described herein, and which can contain polypeptide sequences from other proteins to provide a multivalent vaccine that is effective against different infectious agents. The invention further comprises administering other compositions that can provide a beneficial effect in the animal, which could be administered prior to, concurrently, or subsequent to conventional therapies for such infections.

The invention also provides methods for detecting the viruses disclosed herein. The method comprises obtaining a biological sample from an animal and detecting the presence of a viral protein and/or a viral polynucleotide in or from the sample. Any of the viral polynucleotides and proteins can be used in the method of detecting the presence or absence of the virus. It is considered that detecting the reverse complement or the DNA equivalent of SEQ ID NO:1, 2, or 3, is the same as detecting a polynucleotide comprising the sequence of SEQ ID NO:1, 2, or 3, or a sequence having at least 96% identity to any of those sequences.

Detection can be carried out using any suitable biological sample obtained from a mammal for which a diagnosis is desired. Suitable sources of biological samples include but are not limited to blood, mucosal scrapings, tissue biopsy, or saliva. In one embodiment, the biological sample comprises a nasal and/or a pharyngeal swab, or tracheal wash.

The presence or absence of the virus may be detected by testing for DNA, RNA or protein using a variety of techniques that are well known in the art. In certain embodiments, the presence of the virus is determined by detecting polynucleotides that comprise all or part of the viral genome, or are amplified from all or a part of the viral genome. In this regard, the invention includes determining the presence (or absence) of the virus by identifying polynucleotide sequences from the viral negative strand, the viral plus strand, or combinations thereof. The invention also includes detecting the DNA versions of the viral negative strand, plus strand, and combinations thereof. For example, in one embodiment, the reverse transcriptase polymerase chain reaction can be used to produce a DNA copy of the viral minus strand or a portion of it, and the DNA copy can serve as a template for amplification of the viral genome to obtain a plurality of double stranded DNA molecules that include the DNA version of the plus and minus strands or portions thereof in a hybridized duplex. Those skilled in the art will recognize that there are a wide variety of amplification techniques that can be used to increase the amount of genetic material for use in determining whether a virus is or was in a biological sample of interest, and the amplified (on unamplified) genetic material can be analyzed using many well known techniques and reagents for determining polynucleotide sequences. Thus, the invention includes any and all methods for obtaining and analyzing nucleic acids from a biological sample so that the presence or absence of viral polynucleotides can be ascertained, which include but are not limited to those methods that involve detecting the polynucleotides by hybridization of nucleic acid and/or other types of probes, and by determining the sequence of the viral polynucleotides using any known sequencing technique. All or a portion of the sequence can be determined and be used to identify the viral polynucleotides.

In certain embodiments, the invention provides a composition comprising an isolated viral polynucleotide and components used for nucleic acid hybridization and/or amplification. Accordingly the compositions can additionally comprise a DNA polymerase, a reverse transcriptase, free nucleotide triphosphates, salts, buffers and other reagents typically employed to hybridize and/or amplify nucleic acids. In one embodiment, the invention provides an isolated viral polynucleotide and/or a polynucleotide amplified from a viral polynucleotide, wherein the viral polynucleotide and/or the polynucleotide amplified from the viral polynucleotide is hybridized to one or more amplification primers and detection probes used in real-time nucleic acid amplification techniques.

The invention also provides an isolated viral polynucleotide and/or a polynuceotide amplified from a viral polynucleotide wherein the polynucleotide is hybridized to at least one probe that is present in an array. The array may be present on, for example, a chip used to determine the presence or absence of a plurality of distinct polynucleotides. Such chips are commercially available and can be customized to detect the presence or absence of essentially any polynucleotide.

In various embodiments, the invention further comprises fixing in a tangible medium the determination of whether or not the mammal has been infected by a virus disclosed herein. The tangible medium can be any type of tangible medium, such as any type of digital medium, including but not limited to digitized files that can be stored on a computer, a DVD, a CD-ROM, or an electronic mail message. The tangible medium could be provided to a health care provider so as to develop a treatment protocol for the infected mammal.

It will be recognized by those skilled in the art that, given the benefit of the present invention, a variety of reagents can be made and used in diagnostic methods for detecting the viruses disclosed herein. For instance, polyclonal or monoclonal antibodies can be made using the virions or portions of the virions, or isolated or recombinant viral proteins or fragments thereof. Thus, antibodies can be made to specifically recognize any antigenic determinant present in any of the viral proteins. In various embodiments, the antibodies recognize the NS-1, NS-2, N, P, M, SH, G, F, M2-1, M2-2, and L viral proteins, or portions or combinations thereof. It is expected that antibodies can be made that can discriminate the viruses of the present invention from other related virus, such as MPV.

The antibodies can be used in any technique whereby the presence or absence of a viral antigen in or from a biological sample can be determined. Such techniques include but are not limited to Western blotting, immunofluorescence, immunohistochemistry, and ELISA assays bead-based or conventional protein arrays.

In one embodiment, the invention provides an isolated and/or recombinant virus or virus protein that is present in a complex with an antibody.

The following Examples are meant to illustrate specific embodiments of the invention but should not be construed as limiting the invention in any way.

Example 1

We obtained samples from nasal and pharyngeal swabs from mixed-breed dogs and used to them to inoculate cultures of canine A72 cells (American Type Culture Collection, CRL-1542) to isolate respiratory viruses. At a late stage of passage in culture corresponding to approximately 21 days post-inoculation, some cultures showed subtle cytopathic changes. After continued passage the cultures exhibited small foci of rounded cells followed by rapid cell death throughout the culture. This pattern was subjectively judged to be uncharacteristic of the viruses commonly associated with ARDC. Thirteen individual viral isolates were obtained and are described in this Example. Testing with a panel of diagnostic reagents specific to common canine respiratory agents failed to identify a known virus. Further testing with additional reagents for other viruses ultimately revealed positive recognition by immunofluorescence assay (IFA) using a monoclonal antibody (Mab) pool against human respiratory syncytial virus (anti-HRSV, no. VP-R151, Vector Laboratories, Burlingame, Calif., USA). This antibody preparation is commonly used in our laboratory for the detection of bovine RSV (BRSV). The staining pattern included filamentous membrane-bound and free-floating virions and cytoplasmic inclusions, typical of the pattern observed in RSV-infected cells.

Following the initial IFA results, we attempted to amplify a fragment of the nucleocapsid gene (N) from the virus using PCR primers that were designed based on an alignment of human, bovine and ovine RSV sequences. This was unsuccessful. Stocks of the individual Mabs in the anti-RSV pool and their specificities were obtained from the manufacturer and used for IFA (FIG. 1). Staining with Mab 5H5N (M2 protein-specific) illuminated both virions and inclusions. Mab 2G122 (P protein-specific) stained primarily inclusions and gave a relatively uniform membrane-associated signal. No staining was obtained with Mabs 1C3 (N protein-specific) or 5A6 (F protein-specific). All 4 individual Mabs recognized BRSV by IFA. Recognition of the canine virus by only 2 of 4 Mabs and the inability to amplify a conserved region of the RSV genome suggested that it was related to, but was not a typical form of RSV.

Elucidation of the virus sequence was pursued by designing degenerate PCR primers based on highly conserved amino acid (aa) sequences within multiple sequence alignments of all viruses in the Pneumovirinae subfamily using the CODEHOP algorithm. Specific regions within the L (polymerase) and N genes were targeted. Sequencing of the reaction products and BLAST analysis revealed the virus to be closely related to murine pneumovirus (MPV), traditionally known as pneumovirus (or pneumonia virus) of mice. Two L gene PCR products were found to be 95% to 97% identical to MPV and an N gene fragment was approximately 96% identical.

Figure 2:
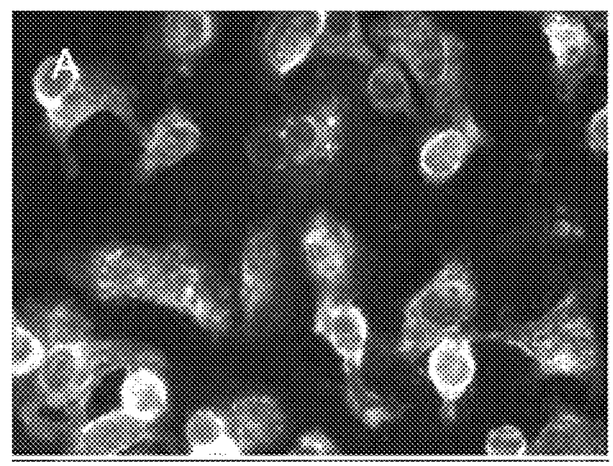
FIG. 2. Immunofluorescence assay showing reactivity of a randomly selected canine serum submitted for non-respiratory related testing against infected and uninfected canine A72 cells. A) Serum on infected cells at a dilution of 1:320. B) Serum on uninfected cells at a dilution of 1:320. The red background is produced by counter-staining with Evan's Blue.
Figure 2:
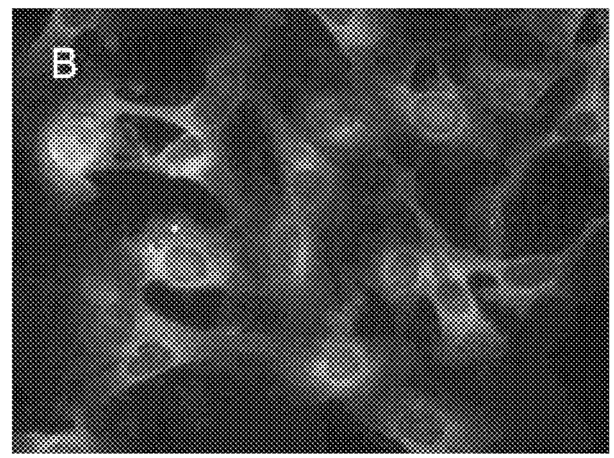

To address the question of whether the newly identified pneumovirus was limited to the group of shelter dogs tested, we screened random canine serum samples and found that 6 of 27 animals had antibodies that specifically recognized the virus in infected cultures. Staining patterns were similar to that observed with the Mabs (FIG. 2). Bovine sera containing variable amounts of neutralizing antibodies against BRSV did not stain cells infected with the canine virus.

This Example demonstrates that the viruses isolated from 13 dogs with ARDC appear to be very closely related to MPV and we therefore consider them to be canine pneumovirus (CnPnV). Murine pneumovirus is one of only three virus species classified in the Pneumovirus genus in the Pneumovirinae subfamily in the family Paramyxoviridae. Human RSV is the type species and it is very closely related to BRSV while MPV is more distantly related. For example, the N protein nucleotide sequences of human and bovine RSV are approximately 94% identical to each other but only have 60% identity to MPV. There are only two fully sequenced strains of MPV, "Strain 15" and J3666, and they are 99.7% identical at the nucleotide level.

The association of CnPnV with ARDC may be pathogenic in some cases, particularly when involved in complex etiologies. By analogy, MPV is commonly known to infect laboratory rodent colonies and serological evidence points to infection of several wild rodent species but little is known about its natural ecology. In fact, it is not clear that rodents are the only natural hosts of MPV or if closely related viruses may be circulating in other species. Evidence for human infection in association with respiratory symptoms has been reported (Pringle C R, et al. J Gen Virol. 1986; 67:975-82). In nature, infection of rodents may be subclinical or latent. Clinical signs in laboratory mice can vary from asymptomatic to progression to pulmonary edema with high morbidity and mortality. Pathogenic strains, including both J3666 and Strain 15, can produce severe pneumonia and death in 6-10 days when inoculated at low dose. The pathogenicity or lack thereof may be virus and mouse strain dependent.

Multiple bacterial and viral agents can be involved in canine respiratory disease. CnPnV is thus considered to be another agent capable of initiating the sequence of events which compromises the defense mechanisms of the upper respiratory tract, leading to more severe disease.

Example 2

The materials and methods presented in this Example were used to obtain the results described in the remaining Examples.

Virus Isolation

Nasal and pharyngeal specimens were collected from mixed breed dogs with respiratory disease signs using moist swabs and were processed within 24 h of receipt at the Animal Heath Diagnostic Center at Cornell University. Prior to inoculation, the swabs were immersed in 3 ml minimum essential medium (MEM) with Earle's salts (Gibco 10370, Invitrogen, Carlsbad, Calif., USA), 0.5% bovine serum albumin, penicillin (200 U/ml), streptomycin (200 μg/ml), and fungizone (2.5 μg/ml) for 30 min and then mechanically agitated for 10 s. Aliquots of the nasal and pharyngeal swab extracts, 0.5 ml each, were combined and used to inoculate a single T25 flask of semi-confluent A72 cells (Binn et al., 1980) (CRL-1542, American Type Culture Collection, Manassas, Va., USA) without additional medium. The extract was allowed to remain on the monolayer for 1-3 h and it was then rinsed off with phosphate buffered saline (PBS). The cells were maintained in 6 ml of culture medium (Leibovitz's L15 medium, 10% heat inactivated fetal bovine serum (FBS), 200 U/ml penicillin, 200 μg/ml streptomycin, 50 μg/ml gentamicin) at 37° C. and sub-cultured every 6-8 days. Uninoculated control A72 cultures were carried in parallel throughout the isolation procedure.

Immunofluorescence Assays

Cells were allowed to attach to glass slides then rinsed with PBS and fixed in cold acetone for 10 min. Slides were air-dried and stored at −20° C. prior to staining Primary and secondary antibodies diluted in PBS were applied to slides and incubated for 30 min at 37° C. After each incubation the slides were rinsed in PBS for 15 min. Staining was visualized by fluorescence microscopy. A Mab pool against HRSV was used in the initial identification (VP-R151, Vector Laboratories, Burlingame, Calif., USA) at a dilution of 1:400. Mouse anti-PVM (CL-603IFA, Charles River Laboratories, Wilmington, Mass. USA) supplied at a 1× concentration was used at a dilution of 1:20. The secondary antibody, FITC-labeled goat anti-mouse IgG (02-18-06, KPL, Gaithersburg, Md., USA), was used at a dilution of 1:40 (12.5 μg/ml).

RNA Purification

Total cellular RNA was purified from A72 cells (74106, Qiagen, Valencia, Calif., USA). Cells from one infected 25 $cm^2$ flask showing approximately 50-75% cytopathic effect (CPE) were pelleted and purified through each column. Cell-free supernatants and medium containing swab eluates were purified (52906, Qiagen) using 140 μl of sample. Purified RNAs were resuspended in 40 μl RNase-free $H_2O$.

PCR

The degenerate primer sequences initially used to obtain genomic fragments were based on alignments of viruses in the Pneumovirinae and were designed using the CODEHOP algorithm (blocks.fhcrc.org/codehop) (Rose et al, 1998). Reverse transcription-PCR (RT-PCR) was performed in a one-step reaction (210212, Qiagen) according to the manufacturer's instructions in a 25 μl volume. One μl of total RNA at a dilution of 1:5-1:10 and 10 pmole of each primer was used per reaction. Reaction conditions for the RT step were 30 min at 50° C. then 15 min at 95° C. Cycling conditions were 60 s at 95° C., 30 s at 54-56° C., and 60-90 s at 72° C. for 35 cycles. Primer sets for N gene: N276F, tccgtgcaggccgaratggarcarg/P1R, (SEQ ID NO:35) ggaactcgggggcgaayttytccat; SEQ ID NO:36); L gene no 1: L428F, ccggatcttcggccayccnatggt/SEQ ID NO:37) L538R, ttcttaggaggggagatggcyttrtcrtt; SEQ ID NO: 38) L gene no. 2: L698F, catcaccgacctgtccaagttyaaycargc/SEQ ID NO: 39) L894R, ttgaagtcgtccaggatggtrttdatcca SEQ ID NO: 40. Two PCR primer sets used with swab samples from various geographic locations were designed based on alignments of the CnPnV, MPV J3666 and strain 15 sequences. G protein: G715F, ggcttctgtttcttcctttctgg/SEQ ID NO: 41) G1062R, ccgtggtggtgcctgtg SEQ ID NO: 42); SH1 protein: SH1F, atggatcctaacatgacctcayac SEQ ID NO: 43)/SH187R, gattgggatgaacygtgcattg SEQ ID NO: 44). Primers used to amplify low passage Brne isolates: G84F, tgtaaaagtgaaccaaatgtgta SEQ ID NO: 45)/G404R, aaatcttcaggtaaatcaggtc SEQ ID NO: 46); G849F, ttttaacaacaagaatcagtc SEQ ID NO: 47)/G1048R, ctcctaggtgcgggggttgg SEQ ID NO: 48). Reaction conditions for the G and SH amplicons were RT at 50° C. for 30 min, inactivation/denaturation at 95° C. for 15 min, and PCR at 60 s at 95° C., 30 s at 54° C., and 90 s at 72° C., for 35 cycles.

Genomic Analysis

PCR products were sequenced using an Applied Biosystems Automated 3730 DNA Analyzer at the Cornell University Sequencing and Genotyping Core Laboratory. Primers used to determine the complete sequences were based on MPV sequences or previously determined CnPnV sequences. Overlapping PCR products were generated to cover gaps and primer binding regions. All regions were sequenced on both strands. CnPnV isolates were compared to the sequences of MPV strain 15 (GenBank AY729016) and J3666 (GenBank NC006579) using Lasergene (DNASTAR, Madison, Wis., USA).

Example 3

Isolation and Identification

Nasal and pharyngeal swab eluates were used to inoculate A72 cells. After a relatively long period in culture, usually appearing after the third or fourth passage, a limited CPE was observed. Initial CPE typically included scattered small foci of rounded cells, sometimes with small syncytia and vacuolization. This CPE progressed slowly over several days in stationary cultures. Subculturing often led to monolayers that maintained this low-grade CPE but in some cultures there was rapid progression and disintegration of the monolayer within 24-48 hours. This pattern, although similar to some herpesvirus infections, did not test positive for canine herpesvirus and did not appear to be typical of any of the canine respiratory viruses that are commonly isolated using similar procedures. Several of the early passage isolates replicated poorly in culture, showing little or no CPE following the transfer of supernatant to fresh cells. However, with continued passage some cultures developed more consistently transferable CPE and they were chosen for further analysis. Initial testing showed that sera from several unrelated dogs appeared to recognize viral antigen in cultures with CPE (data not shown) but tests for common canine respiratory viruses were negative. As reported in Example 1, Mabs specific for HRSV strongly recognized viral antigen. Positive IFA staining with an anti-PVM polyclonal serum was used for confirmation. The anti-PVM mouse serum only weakly recognized BRSV by IFA.

The original 13 isolates of CnPnV described in Example 1 originated from 2 animal shelters that were managed by the same organization. To investigate whether the virus was confined to these 2 locations, nasal or pharyngeal swab specimens from sick dogs from other geographic locations were tested by PCR. Nineteen dogs from 8 states in the USA (CO, GA, FL, IN, MO, NV, SC, VA) were tested using primer sets to the G and SH genes. Of the 19 specimens, one from Nevada, and 5 from a group of 9 dogs from South Carolina, were positive with both G and SH PCRs and were confirmed by sequencing. No PCR positive results were obtained from the other 13 dogs. Virus isolation on A72 cells was attempted on 6 additional nasal swab specimens from New York and Pennsylvania that were submitted for canine respiratory diagnostics. Of these, two additional isolates came from a veterinary hospital in New York City and another originated from a shelter in Philadelphia, Pa. These isolates were confirmed as CnPnV by IFA with anti-RSV and anti-PVM antibodies and subsequently with RT-PCR. While these RT-PCR and virus isolation results do not provide an accurate assessment of prevalence, they do indicate that infection with CnPnV is widespread.

Sequence Analysis

Previous studies have noted differences among viral isolates that may be attributable to the presence of natural quasispecies, mutation during passage in culture, or PCR artifacts. To determine the most accurate consensus sequences for the CnPnV isolates, multiple, overlapping RT-PCR reactions using total cellular RNA as the template were used. Viral isolates from two dogs were sequenced, one at tissue culture passage 4 (Ane4) and one at passage 17 (Brne17), and compared to the sequences of J3666 (Thorpe and Easton, 2005) and strain 15 (Krempl et al., 2005). An 8598 nt sequence (SEQ ID NO:1) was obtained from CnPnV-Ane4 beginning within the 3' leader adjacent to NS1 and extending a short distance into the L coding region, completely covering 9 of the predicted 10 genes in the genome. The gene order NS1-NS2-N-P-M-SH-G-F-M2-L was confirmed. The overall nt sequence identity of this region of CnPnV-Ane4 as compared to the MPV strains was 95.0% to J3666 and 94.7% to strain 15. The MPV strains are 99.7% identical to each other. No gaps were found within the coding regions in comparisons of CnPnV-Ane4 and the MPV strains. With exceptions to length differences for G and SH as described in sections 3.4 and 3.5, all of the coding regions in MPV and CnPnV-Ane4 were found to encode proteins of the same length.

Comparative Analysis of Non-Translated Regions

The boundaries of the GS and GE sequences in CnPnV were determined by alignment to the J3666 and strain 15 sequences (Thorpe, L. C., Easton, A. J., 2005. J. Gen. Virol. 86, 159-169; Krempl, et al. 2005. Virus Genes 30, 237-249). The GS sequences of MPV were described by Chambers et al. (1991) and more recently (Dibben and Easton, 2007) as 9 nt in length based on the RSV GS sequences as determined by Collins et al. (1986). Kuo et al. (1997) provided evidence that the 10th nt is also important in the GS of RSV and this has been equated to an MPV GS as being 10 nt in length (Krempl et al., 2005). In Table 1 the GS is presented as 10 nt to include both interpretations. Table 1 provides sequences of GS, GE and IGRs between coding regions in CnPnV-Ane4 compared to MPV strain 15 and J3666.

TABLE 1

| Gene 3' | GE | IGR | GS | Gene 5' | NTR length |
|---|---|---|---|---|---|
| | | | aggacaagug | NS1 | |
| NS1 | uaguuaauuaaaa | caaagggu | aggacaaauc* | NS2 | no diff. |
| NS2 | uaguuauagaaaaa | uauu* | aggauaaaua | N | no diff. |
| N | uauuuaauuaaaaa (+1[a]) | cuggaaaauau* | aggauaaaua | P | 1 nt longer |
| P | uaguuaauuaaaa | uaac (−3[aca]) | aggacaaaua | M | 3 nt shorter |
| M | uaguuaaauaaaa | c (−1[u]) | aggauaagua* | SH | no diff.* |
| SH | uaguuaacaaaaaa | uu | aggauaagua | G | no diff. |
| G | uaguuaaugaaaaa (+1 [a]) | uaagcuaugauauaau* (−1[c]) | aggacaaaua | F | no diff. |
| F | uaguuaauuaaaaaa (+1[a]) | cuu[b] | aggauaagug[b] | M2 | 1 nt longer |
| M2 | uaguuauauaaaaa (−2[a]) | uaaucaauu* | aggaucaaua | L | 2 nt shorter |

For Table 1, there are no differences in NTR lengths between the two MPV strains. RNA sequences are in 5' to 3' orientation. *: Indicates at least 1 nt change from J3666 and strain 15. nt differences are in bold and underlined. GE: gene end; IGR: intergenic region; GS: gene start; no diff; no differences in length. [a]For M-SH there is no difference in overall NTR length; one u is deleted from the IGR and another u is added upstream in the NTR. [b]The 3 nucleotide IGR and likely M2 GS is based on analysis by Dibben and Easton (Dibben, O., Easton, A. J., 2007. Mutational Analysis of the Gene Start Sequences of Pneumonia Virus of Mice. Virus Res. 130, 303-309). Sequences having 10 or more nucleotides shown in Table 1 have the following SEQ IDs: For the sequences in the "GE" column: NS1 uaguuaauuaaaa (SEQ ID NO:18); NS2 uaguuauagaaaaa (SEQ ID NO:19); N uauuuaauuaaaaa (SEQ ID NO:20); P (SEQ ID NO:18); M uaguuaaauaaaa (SEQ ID NO:21); SH uaguuaacaaaaaa (SEQ ID NO:22); G uaguuaaugaaaaa (SEQ ID NO:23); F uaguuaauuaaaaaa (SEQ ID NO:33); and M2 uaguuauauaaaaa (SEQ ID NO:34). For the sequences in the "IGR" column: N cuggaaaauau (SEQ ID NO:24); and G uaagcuaugauauaau (SEQ ID NO:25); For the sequences in the "GS" column; NS1 aggacaagug (SEQ ID NO:26; NS2 aggacaaauc (SEQ ID NO:27); N aggauaaaua (SEQ ID NO:28); P (SEQ ID NO:28); M aggacaaaua (SEQ ID NO:29); SH aggauaagua (SEQ ID NO:30); G (SEQ ID NO: 30); M2 aggauaagug (SEQ ID NO:31); F (SEQ ID NO:29) and L aggaucaaua SEQ ID NO:32).

A few length variations and nt differences were identified in the CnPnV-Ane4 NTRs, the majority found within the IGRs. There are no differences between the two MPV strains in the IGRs. Chambers et al. (Chambers, P., Matthews, D. A., Pringle, C. R., Easton, A. J., 1991. Virus Res. 18, 263-270) determined the GS of M2 from a cDNA clone but also noted the presence of 2 additional potential GS sequences (GS1 and GS2) in the 56 nt IGR. Mutational analysis later determined that the putative GS sequence was non-functional due to G instead of A at position 6. Subsequently, they determined that both the GS1 and GS2 sequences were capable of directing transcriptional initiation with the first sequence (GS1) being most important. They concluded that the originally identified GS sequence was misidentified likely due to a spontaneous deletion during cDNA cloning. In CnPnV the GS1 sequence for M2 that immediately follows the GE sequence for F is identical to the SH and G gene start sequences except at the 10th nt. It is believed that GS1 is used primarily and it is shown in Table 1. The GS2 for M2, AGGACAGGG, differs at only 2 positions from the consensus sequence reported in (Dibben, O., Easton, A. J., 2007. Virus Res. 130, 303-309) but may have limited activity because it does not have a conserved A at position 7. This differs from J3666 and strain 15 where the A is conserved. The third potential M2 GS (GS3) in CnPnV-Ane4 is identical to that of J3666 and strain 15 and is therefore presumed to be poorly-functional due to the G at position 6.

Analysis of Non-Structural Proteins

The non-structural small hydrophobic protein appears to tolerate significant variability as it is the most divergent protein between the two MPV strains where there is only 92.4% aa identity over the 92 aa that they share. In CnPnV-Ane4 the SH protein was the most divergent of all of the proteins examined when compared to MPV strain 15. CnPnV-Ane4 SH has 4 aa differences (95.7%) with J3666 and 9 aa differences (90.2%) with strain 15 and is therefore more similar to J3666 than the MPV strains are to each other (Table 2). Another significant difference is in the length of the SH ORF in different isolates. Both CnPnV-Ane4 and strain 15 have SH ORFs of 279 nt (92 aa) whereas the published J3666 SH sequence is 345 nt (114 aa). However, it has been reported that independently amplified sequences of J3666 coded variously for 92, 96, or 114 aa and suggested that these represented antibody escape mutants. Table 2 provides a summary of percent identity of CnPnV-Ane4 genes and proteins to viruses in the Pneumovirinae subfamily.

TABLE 2

| Gene | MPV-J3666 nt/aa (Δnt/Δaa)[a] | MPV-strain 15 nt/aa (Δnt/Δaa) | HRSV nt/aa | BRSV nt/aa | HMPV nt/aa | AMPV nt/aa |
|---|---|---|---|---|---|---|
| NS1 | 94.4/93.8 (18/7) | 94.4/93.8 (18/7) | 44.1/15.0 | 43.4/15.9 | NA | NA |
| NS2 | 95.1/94.2 (23/9) | 95.1/94.2 (23/9) | 42.6/22.6 | 42.6/22.6 | NA | NA |
| N | 95.9/97.7 (48/9) | 96.0/98.0 (42/8) | 61.1/59.6 | 61.4/60.4 | 51.7/45.2 | 50.3/42.6 |
| P | 95.0/96.6 (44/10) | 94.3/94.4 (1/15) | 49.9/41.9 | 48.8/44.4 | 40.8/29.1 | 40.4/29.1 |
| M | 96.6/98.1 (27/5) | 96.5/98.1 (28/5) | 54.6/41.6 | 54.4/42.0 | 51.4/39.1 | 50.5/39.1 |
| SH | 93.2/95.7 (19/4) | 91.0/90.2 (25/9) | 44.7/18.5 | 39.7/16.0 | 31.5/6.6 | 29.3/12.0 |
| G | 94.5/91.9 (66/32) | 94.5/91.7 (65/33) | 33.4/19.4 | 37.1/14.4 | 36.7/10.5 | 33.2/10.7 |
| F | 97.1/97.4 (47/14) | 97.0/97.0 (49/16) | 54.6/43.6 | 55.0/45.3 | 50.9/40.8 | 49.8/41.0 |
| M2-1 | 95.5/96.6 (24/6) | 95.5/96.6 (24/6) | 53.5/42.6 | 52.4/42.0 | 47.0/36.0 | 48.7/36.0 |
| M2-2 | 96.3/95.9 (11/4) | 96.3/95.9 (11/4) | 37.3/11.1 | 39.9/12.2 | 34.0/5.6 | 34.9/9.9 |

For Table 2, references to sequence GenBank no: HRSV, NC_001781; BRSV, NC_001989; HMPV, NC_004148.2; AMPV, NC_007652, which correspond to full length sequences of human RSV, bovine RSV, human metapneumovirus and avian metapneumovirus. nt: nucleotide; aa: amino acid; NA: not applicable. [a]numbers of nt and aa differences in each gene. The CnPnV-Ane4 P protein was found to have 10 aa differences with J3666 and 15 aa differences with strain 15. Alignments of MPV and RSV P show two regions of high homology flanking an amino-proximal region from aa 22 to 124 that has no obvious similarity and contains 6 to 7 gaps in the alignment. Two regions of moderate diversity were identified within this region of low homology in P when CnPnV-Ane4 was compared to both MPV strains. Seven aa differences are clustered in the aa 58-74 region and another 4 changes are found at aa 93-102. Probability plots predict the first region of diversity from aa 58-74 to have a relatively high surface probability and antigenic index. The second diverse region at aa 93-102 is hydrophobic and has low predicted surface probability (data not shown). A second overlapping internally-initiated ORF in P, capable of encoding a protein of 137 aa, has been identified in MPV. Synthetic mini-genomes constructs were used to study the protein produced from the second ORF and it was found to function as a transcription inhibitor. CnPnV-Ane4 has the second overlapping P ORF initiating at the same position but it terminates earlier and yields a protein of less than half the size at 54 aa due to a T to A transversion at nt 285 producing a TAG codon. (Dibben, O., et al. (2008) Virus Res. 131, 47-53). This leaves open the question as to whether a shorter P-2 protein, if produced, has the same functionality.

The remaining non-structural proteins include NS1 and NS2, and M1-1 and M1-2 which are translated from alternate reading frames in the M2 gene. There are no differences between these proteins in strain 15 and J3666. However, CnPnV has differences with the MPV isolates in each of these proteins. CnPnV-Ane4 NS1 has 7 aa differences compared with the two MPV strains, 4 located near the C-terminal end. In NS2 there are 9 aa differences that are relatively evenly distributed throughout the sequence. CnPnV-Ane4 is 96.6% identical to M2-1 with 6 aa differences and 95.9% identical to M2-2 with 4 aa differences.

Analysis of Structural Proteins

The G attachment proteins of pneumoviruses are of special interest because they are typically the most divergent and are primary targets for neutralizing antibody responses. The G protein is relatively highly conserved between the two MPV isolates having only 3 differences out of 396 aa (99.2%). In CnPnV the G protein is the least conserved protein in comparison to J3666 and the second least conserved after SH in strain 15. There are 32 aa and 33 aa differences with J3666 and strain 15 G respectively. The aa differences are generally randomly distributed with the exception of several differences clustered in the 113-124 region and 11 aa differences between aa 331 and 367 (based on the numbering of the Ane4 ORF). One notable observation is that the G ORF of CnPnV-Ane4 is 54 nt longer than its counterpart in J3666 and strain 15. An ACG to AUG change at position +29 from the GS creates an alternative initiation codon that is present in J3666 but not in strain 15. A second UAG to AAG change at +65 eliminates an in-frame termination codon. The G ORF encodes for a protein with a cytoplasmic tail of 53 aa, 18 aa longer than the published J3666 and strain 15 sequences. The sequence of J3666 has a termination codon at this position while strain 15 does not. Therefore, in both J3666 and strain 15 a single point mutation could produce the longer G variant. This is not unprecedented as the sequence of uncloned RT-PCR product amplified from the lungs of J3666-infected mice also had the U to A change at +65. It therefore, appears that the longer variant of G is not a feature that is unique to CnPnV. Given the benefit of the present disclosure, additional sequence data from canine and murine RT-PCR products to determine which variation predominates in natural infections can be determined using ordinary skill in the art. There appears to be some natural plasticity in the length of the G cytoplasmic tail and that the tail is itself a determinant of virulence. A recombinant MPV mutant lacking the G cytoplasmic tail was attenuated in BalbC mice but levels of replication were indistinguishable from wild-type virus (Krempl, C. D., et al. 2007. J. Virol. 81, 9490-9501). In RSV the first 6 aa of the cytoplasmic tail are essential for interaction with the M protein. It is not known if the N-proximal aa of G are essential for binding to M in MPV, but if it proves to be the case then the two variations of the cytoplasmic tail might differ in their ability to interact with M.

The F protein of CnPnV-Ane4 does not have a similar high level of diversity as is found in G and in fact it is one of the more conserved proteins in comparison to MPV. There are 14 aa differences with J3666 and 16 aa differences with strain 15 with 97% or greater conservation. Approximately one-half of the aa differences are within the final 55 aa at the COOH-terminal end, within or adjacent to the transmembrane domain, and most of the aa substitutions are of similar functional group type. Overall, N is the most highly conserved protein in relation to the other pneumoviruses. The central region of the protein from aa 245-333 in CnPnV-Ane4 reaches 92 to 93% identity with HRSV and BRSV. CnPnV-Ane4 N has 9 aa differences with J3666 and 8 differences with strain 15 that are relatively evenly distributed. None of the aa differences correspond to the invariant positions identified in the pneumoviruses or to the residues that interact with the RNA genome. It seems unlikely that any of these differences would have a significant effect on protein structure or function. The M protein has the highest level of conservation with the MPV isolates at 98.1%. The 5 aa differences are distributed evenly in the sequence and in every case the functional groups are conserved. Only one difference, a V to I change at aa 18, involves a residue that is normally found to be invariant in the M protein of pneumoviruses and metapneumoviruses.

Analysis at High and Low Passage in Culture

We identified one isolate to be well adapted to culture and consistently replicated and produced CPE when used to infect naïve cultures. Although this isolate was at passage 17 (Brne17), it was sequenced and subsequently compared to the lower passage Ane4 isolate. Of the 8423 nt sequenced, 7 nt differences were identified in Brne17 (Table 3, provides nucleotide and amino acid differences between CnPnV-Ane4 and Brne at two stages of passage and ex vivo.) For Table 3, [a]Nucleotide position from the beginning of each gene start. [b]Amino acid numbering based on the position in each ORF. ND: not determined; nt: nucleotide; aa: amino acid.

TABLE 3

| Gene | Position | Ane4 | Brne17 | Brne3 | BrneSw |
|---|---|---|---|---|---|
| N | nt 1081[a] | T | C | ND | ND |
| | — | — | — | | |
| M | nt 543 | A | G | ND | ND |
| | aa 178[b] | Q | R | | |
| SH -G NTR | nt 397 | — | +A | ND | ND |
| | — | — | | | |
| G | nt 392 | A | T | T | A |
| | aa 122 | K | stop | stop | K |
| G | nt 1053 | T | C | T | ND |
| | aa 342 | L | P | L | |
| F | nt 1098 | A | T | ND | ND |
| | — | — | — | | |
| F | nt 1140 | G | A | ND | ND |
| | — | — | — | | |

A single nt difference in N and 2 differences in F are synonymous substitutions. The addition of an A residue in the SH GE sequence in Brne17 is also non-coding. Two nt differences are non-synonymous substitutions causing a Q to R change at aa 178 in M and an L to P change at aa 342 in G. The most significant difference found in Brne17 is the substitution of a U for an A at nt 364 in the G ORF which results in replacement of a K residue with a termination codon at aa position 122. This position corresponds to nt 310 (aa 104) in the MPV strains. Termination at this position would give Brne17 a truncated G with a cytoplasmic tail of 53 aa, a transmembrane domain of 24 aa, and an ectodomain of only 44 aa. The finding of a truncated G in Brne17 prompted additional sequencing of amplification products from passage 3 stock and from the original swab eluate (Brne3 and BrneSw). Interestingly, this showed that the truncated variant was already established as early as passage 3. However, in BrneSw there was an A at nt 364 indicating that the predominant viral species in the dog did not have a truncated G. A second independent set of RNA extractions and amplifications included samples from passages 1 and 2 and only in passage 1 was there an underlying peak on the electropherogram indicating a minor subpopulation with A at nt 364. Thus, it appears that the truncated form was rapidly selected for in culture. A similar mutation was identified in the culture passaged strain 15 (Warwick) where a single nt insertion creating a frameshift causes premature termination of the peptide. Translation initiating at an alternate downstream site can still produce a G protein that is 33 aa shorter and lacks a cytoplasmic tail. The truncated G has been suggested as at least a partial explanation for the reduced virulence of strain 15 (Warwick).

In RSV, the cold-passaged cp-52 mutant was found to have a large deletion that eliminated production of both G and SH but did not prevent replication in culture. The situation is analogous in MPV since a recombinant lacking the entire G gene replicated as well as complete recombinant virus in BHK-21 cell cultures but did not replicate to detectable levels in mice. This suggests that G is always essential in vivo and therefore the detection of only the non-truncated variant in BrneSw would be expected. Why there appeared to be complete selection of the truncated variant by the end of passage 2 is not clear. If selection is simply due to increased efficiency of replication then it would be expected that the absence of G increases replication rate and titer, but there is no supporting evidence that this is the case (Krempl et al., 2007, supra). Factors affecting selection of G deletion mutants may be specific to A72 cells.

Figure 3:
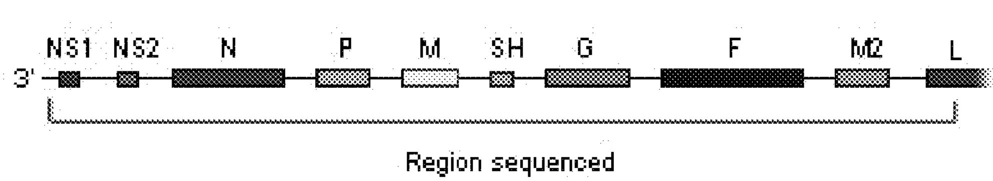
FIG. 3. A graphical representation of the organization of a viral genome comprising the sequence of SEQ ID NO:1.

FIG. 3 provides a graphical representation of the genome organization of SEQ ID NO:1. Those skilled in the art will recognize that the graphic in FIG. 3 is shown in the 3' to 5' orientation because it is a negative strand virus, while SEQ ID NO:1 presents the minus strand in 5' to 3' reading from left to right per conventional orientation. Thus, in FIG. 3, the L ORF is at the 3' end of the plus strand. Table 4 provides an annotation of the sequence presented in SEQ ID NO:1; abbreviations are: GS, gene start signal sequence; ORF, open reading frame; GE, gene end signal sequence; IGR, non-transcribed intergenic region. Unlisted nucleotides are believed to be untranslated.

TABLE 4

| | |
|---|---|
| 3' leader | 1-25 |
| NS1-GS | 26-35 |
| NS1-ORF | 64-405 |
| NS1-GE | 423-435 |
| IGR | 436-443 |
| NS2-GS | 444-453 |
| NS2-ORF | 457-927 |
| NS2-GE | 1001-1014 |
| IGR | 1015-1018 |
| N-GS | 1019-1028 |
| N-ORF | 1050-2231 |

TABLE 4-continued

| | |
|---|---|
| N-GE | 2225-2238 |
| IGR | 2239-2249 |
| P-GS | 2250-2259 |
| P-ORF | 2259-3146 |
| P-GE | 3144-3156 |
| IGR | 3157-3160 |
| M-GS | 3161-3170 |
| M-ORF | 3171-3944 |
| M-GE | 4080-4092 |
| IGR | 4093 |
| SH-GS | 4094-4103 |
| SH-ORF | 4104-4382 |
| SH-GE | 4476-4489 |
| IGR | 4490-4491 |
| G-GS | 4492-4501 |
| G-ORF | 4520-5764 |
| G-GE | 5812-5825 |
| IGR | 5826-5841 |
| F-GS | 5842-5851 |
| F-ORF | 5851-7464 |
| F-GE | 7490-7504 |
| IGR | 7505-7507 |
| M2-GS | 7508-7517 |
| M2-1-ORF | 7564-8094 |
| M2-2-ORF | 8028-8324 |
| M2-GE | 8420-8433 |
| IGR | 8434-8442 |
| L-GS | 8443-8452 |
| L-ORF | 8452-8598 |

Example 4

We also analyzed biological samples obtained from felines for the presence of viruses that could be related to the canine virus identified herein. Sequences were obtained for two isolates, termed 29 Kentucky (29 KY) and 77 Kentucky (77 KY). Partial G gene sequences from 29 KY and 77 KY provide 353 nt corresponding to nt 726-1078 in the canine pneumovirus (CnPnV) Ane4 isolate described above and partial SH gene: 29 KY having 207 nt corresponding to nt 2-208 in CnPnV-Ane4.

The partial G nucleotide sequence of both isolates is 94.7% identical to murine pneumovirus (MPV) isolate J3666 and 98.0% identical to Ane4. The 117 amino acid (aa) sequence is 90.6% identical to J3666 and 97.4% identical to Ane4. Thus, the feline 29 KY/77 KY G sequences are more related to Ane4 than to J3666.

The partial SH nt sequence of 29 KY is 94.7% identical to J3666 and 97.1% identical to Ane4. The 69 aa sequence is 98.5% identical to J3666 and 97.1% identical to Ane4. Thus, the feline 29 KY sequence is slightly more related to J3666 than to Ane4. Nevertheless, it is considered that these sequences represent newly discovered feline pneumoviruses. Thus, the description of compositions and methods and all embodiments of the invention described for the canine pneumoviruses as set forth above apply to the feline viruses as well and those descriptions are therefore reiterated for the feline virus.

Those skilled in the art will recognize from the foregoing that we have demonstrated that CnPnV infection is not limited to dogs in the shelters from which it was originally isolated. It has been readily identified in specimens from dogs with acute respiratory disease. While a causative role in disease has not been definitively proven, the present invention has provided compositions and methods for identifying the presence of the virus and protecting against it, which are expected to be important in controlling respiratory disorders in mammals, including but not necessarily limited to such disorders in both felines and canines that are positively correlated with the presence of the virus.

We claim:

1. An isolated DNA polynucleotide that is a complementary DNA (cDNA) of a polynucleotide that is at least 96% identical to the sequence of SEQ ID NO: 1, 2 or 3.

2. The isolated cDNA polynucleotide of claim 1, wherein the isolated cDNA is complementary to a polynucleotide that is at least 96% identical to the sequence of SEQ ID NO: 1.

3. The isolated cDNA polynucleotide of claim 1, wherein the isolated cDNA is complementary to a polynucleotide that is at least 96% identical to the sequence of SEQ ID NO: 2.

4. The isolated cDNA polynucleotide of claim 1, wherein the isolated cDNA is complementary to a polynucleotide that is at least 96% identical to the sequence of SEQ ID NO: 3.

* * * * *